(12) United States Patent
Gratzl et al.

(10) Patent No.: US 7,521,020 B2
(45) Date of Patent: Apr. 21, 2009

(54) DEVICE FOR PRECISE CHEMICAL DELIVERY AND SOLUTION PREPARATION

(75) Inventors: Miklos Gratzl, Mayfield Heights, OH (US); Koji Tohda, Mayfield Heights, OH (US); George Rozakis, Lakewood, OH (US)

(73) Assignee: Case Western Reserve University, Cleveland, OH (US)

( * ) Notice: Subject to any disclaimer, the term of this patent is extended or adjusted under 35 U.S.C. 154(b) by 916 days.

(21) Appl. No.: 10/682,168

(22) Filed: Oct. 9, 2003

(65) Prior Publication Data

US 2004/0147042 A1  Jul. 29, 2004

Related U.S. Application Data

(63) Continuation-in-part of application No. 09/980,089, filed as application No. PCT/US00/14805 on May 30, 2000, now abandoned.

(60) Provisional application No. 60/460,082, filed on Apr. 3, 2003, provisional application No. 60/417,149, filed on Oct. 9, 2002, provisional application No. 60/137,134, filed on May 28, 1999.

(51) Int. Cl.
*B01L 3/02* (2006.01)

(52) U.S. Cl. .................. 422/100; 422/99; 73/863; 436/180

(58) Field of Classification Search .......... 422/99–101; 73/863; 436/180; 424/468
See application file for complete search history.

(56) References Cited

U.S. PATENT DOCUMENTS

| | | | |
|---|---|---|---|
| 3,993,072 A * | 11/1976 | Zaffaroni | 424/430 |
| 4,837,161 A | 6/1989 | Stevens et al. | |
| 5,008,112 A * | 4/1991 | DePrince et al. | 424/468 |
| 6,048,457 A * | 4/2000 | Kopaciewicz et al. | 210/321.6 |
| 6,050,150 A | 4/2000 | Underhill et al. | |
| 6,599,754 B2 | 7/2003 | Miller et al. | |

* cited by examiner

*Primary Examiner*—Jill Warden
*Assistant Examiner*—Jyoti Nagpaul
(74) *Attorney, Agent, or Firm*—Tarolli, Sundheim, Covell & Tummino LLP

(57) ABSTRACT

A burette (10, 110, 200) suitable for delivery of a reagent into a target solution (50) employs diffusion for delivering the reagent. The reagent is in the form of a solution, which is combined with a matrix material (22), such as a gel or porous ceramic. A membrane (32) covers a delivery outlet (20) to the burette. In one embodiment, the delivery outlet comprises a plurality of fine bores (36), each one filled with or covered by a membrane (38). Stirring of the burette or target solution is achieved with a stirring means (104, 106). A heating or cooling means (80) heats a tip (16) of the burette.

16 Claims, 18 Drawing Sheets

DEVICE FOR PRECISE CHEMICAL DELIVERY AND SOLUTION PREPARATION

This application claims the benefit of U.S. Provisional Application Ser. No. 60/417,149, filed Oct. 9, 2002, U.S. Provisional Application 60/460,082, filed on Apr. 3, 2003, and is a continuation-in-part of U.S. patent application Ser. No. 09/980,089, filed on Jun. 26, 2003 now abandoned, and claims the benefit of PCT Application Serial No. PCT/US00/14805, filed May 30, 2000, and U.S. Provisional Application Ser. No. 60/137,134, filed May 28, 1999, from which U.S. patent application Ser. No. 09/980,089 claims priority, the specifications of all of which are incorporated herein in their entireties, by reference.

BACKGROUND OF THE INVENTION

1. Field of the Invention

The invention relates to a device and method for forming solutions. In particular, it relates to a diffusional burette for controlled delivery of chemicals and biochemicals into a target material, such as a liquid, and will be described with particular reference thereto.

2. Discussion of the Art

Currently available methods for reagent and solution preparation involve the use of traditional tools, such as analytical balances and glassware, including beakers of different sizes, pipettes, and burettes.

Such tools are suitable for preparing reagents and solutions of relatively large volumes, in the milliliter range. However, a demand has arisen for delivery devices which are capable of delivering liquid volumes which are up to several orders of magnitude smaller, to reduce waste and associated costs, and also to accommodate the ever increasing sensitivity of the instrumentation techniques that use these reagents and solutions. To satisfy the emerging needs for solution preparation in the microliter (µL) volume range, pipettes based on liquid displacement by a precisely controlled volume of air have been introduced. For example, Eppendorf-type pipettes which use air/gas pressure and air/gas displacement for volumetric reagent transfer and delivery are now in use.

These devices deliver fixed or adjustable volumes of aqueous reagents from disposable plastic pipette tips by aspirating an appropriate volume of source solution into the tip and then delivering it into a target solution by reversing the air flow. A piston-type arrangement, inside the pipette body, whose air volume is precisely controlled, is used to meter the liquid volume that is aspirated into the tip, and subsequently delivered in one shot into the target solution.

For continuous (as opposed to bolus type) reagent delivery, mechanized piston burettes have been introduced, where a stepping motor controls the reagent volume aspirated, as well as delivered. Such mechanized burettes cover the microliter (mL) as well as µL ranges in terms of delivered volume. For delivering sub-µL volumes, different mechanized schemes have been conceived, such as a vibrating cantilever that "shoots" nanoliter (nL) droplets into the target across air.

While such novel pipette and burette designs reach into the µL volume ranges, the mechanical working principles do not facilitate their adaptation to the handling of even smaller target liquid volumes or smaller reagent increments delivered. One constraint for the pipettes is evaporation, which becomes significant, even during short periods of time, for droplets smaller than about 1 µL. Adjusting sub-µL air volumes accurately and precisely is also difficult. Moreover, dislodging a nL-size droplet from a pipette tip is often difficult, since capillary forces become stronger relative to droplet mass as the droplet size decreases. Thus, accuracy and precision for the delivery of sub-µL volumes by a pipette based on air displacement is not readily achieved.

Furthermore, preparation of solutions of relatively low concentrations often involves multiple steps that are difficult to perform with high final accuracy and precision. The first step is, typically, weighing a very small mass of solid (crystalline or powdered) material, i.e., the chemical that is to be present in the final solution, on an analytical balance. This, often tiny, amount of material may be hygroscopic (i.e., it absorbs water from humidity in air). This tends to falsify the weighed amount. Additionally, a powdery material may tend to float in air, contaminating the balance and the environment. The chemical may also be hazardous, posing problems to the user. The weighed material is then transferred into a beaker. These steps, requiring utmost care, are often sources of significant errors that propagate through all subsequent steps. Typically, multiple dilutions follow, until the desired low concentration is achieved. Further errors tend to be added in each step. In addition, such a procedure is labor intensive and prone to mistakes. Moreover, the process of serial dilution frequently uses far more of the raw material than is needed in the final solution than is needed, resulting in wastage of often expensive materials or hazardous waste production.

The mechanized burettes suffer similar drawbacks when sub-µL volumes are to be delivered in a continuous fashion. Accuracy and precision of the displaced reagent volume become worse as the delivered volume decreases, especially in the nL volume range. Parasitic diffusion between the burette tip and the target liquid may add errors that are difficult to estimate, and even more difficult to correct. On the other hand, if the burette tip is not in direct contact with the target liquid, droplets form at the tip that must be dislodged to reach the target. Thus, delivery by the burette becomes effectively discrete.

The present invention provides a new and improved reagent delivery device and method of use and fabrication which overcome the above-referenced problems and others.

SUMMARY OF THE INVENTION

In accordance with one aspect of the present invention, a delivery device for delivering a reagent into a target material is provided. The delivery device includes a body which defines an interior chamber and a delivery port fluidly connected with the chamber. The chamber holds a reagent in solution. A reagent permeable membrane is provided through which reagent passes into the target material when the delivery port is in fluid communication with the target material. Substantially no volume change occurs in the target material during delivery of the reagent to the target material.

In accordance with another aspect of the present invention, a method of forming a target solution is provided. The method includes loading a reagent solution into a chamber fluidly connected with a delivery port. The delivery port is fluidly contacted with a target liquid for a period of time such that the reagent diffuses from the chamber through a porous material and delivery port into the target liquid to form the target solution.

In accordance with another aspect of the present invention, a diffusional burette for delivery of a reagent into a target material is provided. The burette includes a body which defines an interior chamber for receiving the reagent and a delivery port fluidly connected with the chamber, the delivery port defining a plurality of holes, each of the holes having a cross sectional width of less than 500 microns. A reagent permeable matrix material is disposed within the body. A solution of the reagent is in the chamber, such that the reagent diffuses from the chamber via the holes into the target material when the delivery port is in fluid communication with the target material.

As used herein, "delivery time" means the period of time in which a diffusional burette is in fluid contact with a target material such that a reagent passes from the diffusional burette to the target material.

An advantage of at least one embodiment of the present invention is that non-volumetric (non-convective) reagent delivery is used for transfer of chemicals. As a result, substantially no volume changes are induced in the target solution.

Another advantage of at least one embodiment of the present invention is that it enables automatic delivery to be achieved using natural processes that are spontaneously occurring during delivery.

Another advantage of at least one embodiment of the present invention is that the delivered amount may be controlled by monitoring the delivery time. Delivery time can be controlled extremely precisely using readily available techniques.

Another advantage of at least one embodiment of the present invention is that ranges of delivery rates are adjustable by varying the concentration of a chemical in a burette and by varying the geometrical dimensions of the burette.

Another advantage of at least one embodiment of the present invention is that high reproducibility and precision are achieved easily and cost effectively. As a consequence, waste disposal costs and reagent costs are minimized.

Another advantage of at least one embodiment of the present invention is that very low target solution volumes and delivery rates are feasible, enabling preparation of reagents of extremely low concentrations and/or volumes.

Another advantage of at least one embodiment of the present invention is that preparation of a reagent or solution can be achieved in one single step, without the need for serial dilutions.

Another advantage of at least one embodiment of the present invention is that a target solution can be prepared with multiple reagents by introducing the reagents simultaneously or sequentially.

Another advantage of at least one embodiment of the present invention is that it enables high precision and accuracy of the resulting reagent or solution to be achieved.

Another advantage of at least one embodiment of the present invention is that natural processes of diffusion, capillary forces, and surface tension, which affect delivery rates, are extremely reproducible, where other conditions are kept the same or accounted for, such as geometry, pressure, and temperature.

Another advantage of at least one embodiment of the present invention is that operator errors are minimized.

Another advantage of at least one embodiment of the present invention is that co-delivery of several chemicals is possible in a single step, thus leading to one step production of complex mixtures.

Another advantage of at least one embodiment of the present invention is that parallel processing of several or many deliveries into several or many solutions is feasible with little human control.

Another advantage of at least one embodiment of the present invention is that the delivery methods are amenable to microfabrication and MEMS technologies for serial production.

Another advantage of at least one embodiment of the present invention is that both aqueous and non-aqueous solutions can be prepared, using both aqueous and non-aqueous reagent sources.

Another advantage of at least one embodiment of the present invention is that the provision of a suitable membrane and/or matrix material inhibits convection or flow through a delivery port, such that a reagents is transported through the port primarily by diffusion.

Another advantage of at least one embodiment of the present invention is that it enables delivery to be achieved without moving mechanical parts.

Still further advantages of the present invention will be readily apparent to those skilled in the art, upon a reading of the following disclosure and a review of the accompanying drawings.

DETAILED DESCRIPTION OF THE PREFERRED EMBODIMENT

Figure 1:
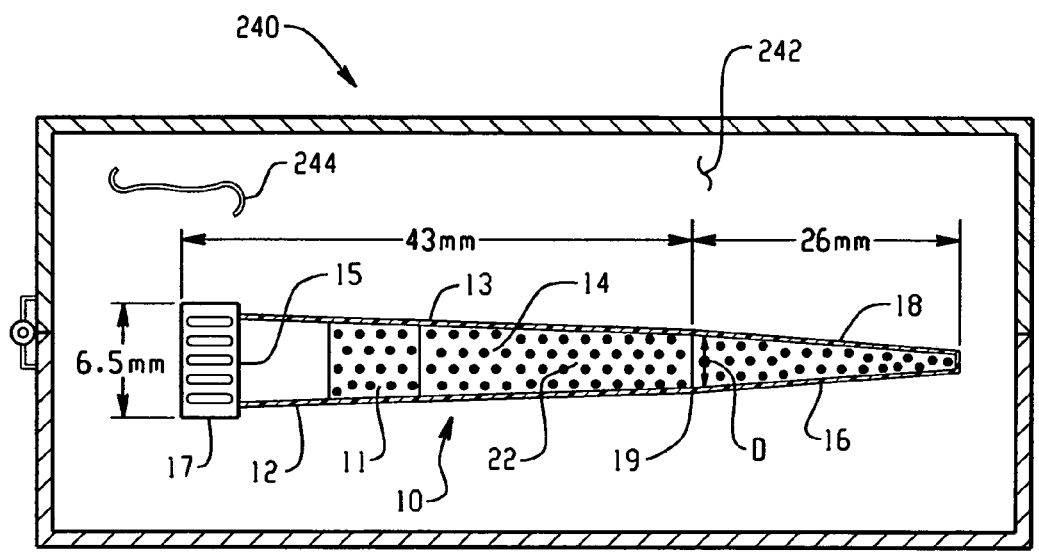
FIG. 1 is a schematic side sectional view of one embodiment of a delivery device in a storage holder according to the present invention.

With reference to FIG. 1, a delivery device in the form of a diffusional burette 10 suitable for the delivery of a chemical, chemical species, biological, or biochemical species or molecule (hereinafter referred to generally as a "reagent") to a target material or vessel is shown.

The target material is one which, on fluid contact with the burette 10, allows the reagent to be taken up or absorbed by the target material. Suitable target materials include liquids, such as water, aqueous solutions, and organic solvents, porous solid materials, such as medicament carriers, ceramics, and the like, absorbent fibers, semisolid materials, such as gels, and combinations thereof. While the target material will generally be referred to as being a liquid, it will be appreciated that other target materials are also contemplated.

Exemplary reagents include laboratory reagents, such as acids; bases; ions, e.g., alkali metal and alkaline earth metal ions, halide ions, and the like, such as potassium ions and bromide ions; reducing and oxidizing agents and agents that can be reduced or oxidized, such as ascorbic acid and permanganate ions, ferricyanide, ferrocyanide; drugs; pharmaceuticals; antigens; antibodies; protein molecules; and the like. The reagent is preferably in the form of a solution 11, which can be aqueous or nor aqueous. When the reagent diffuses into the target solution, it may form a target solution containing the reagent. Or, the reagent may undergo a reaction to produce a second species. Thus, the target solution need not contain the reagent or may contain less reagent than the amount actually diffused.

While the reagent is generally described in terms of a single chemical or species, it will be appreciated that a single burette 10 may deliver two or more reagents at the same time. These reagents may be in similar or different concentrations, according to the desired end use of the burette and either mixed together or separately contained within the burette.

The burette 10 of FIG. 1 includes a body or casing 12, formed from glass, plastic, ceramic, or other suitable material which is preferably impermeable to and unreactive toward the reagent and its solution. The body is preferably impermeable to and unreactive toward the target material. The body 12 includes a reagent holding portion 13, which defines an interior chamber 14 that holds a quantity of a reagent in solution, introduced via an opening 15 at one end of the chamber 14. The body also includes a tip portion 16, in fluid communication with the other end of the chamber 14, through which the reagent is delivered from the burette. The shape of the tip portion 16 affects the delivery, as will be described in greater detail below. A cap 17 or other sealing member closes off the opening 15 to the reagent holding portion 14 after filling with the reagent. Intermediate the tip portion 16 and the reagent holding portion 13 is optionally a shoulder portion 18. The shoulder portion may be conical and have an internal diameter D at its widest end 19 which is wider than the diameter d of a delivery port 20 in the tip 16. As shown in FIG. 1, the reagent holding portion 13, shoulder 18, and tip 16 are integrally formed, with the shoulder being simply an extension of the tip, although other configurations are also contemplated. FIG. 1 provides exemplary dimensions for the burette 10, although it will be appreciated that burettes of different sizes are readily formed. Preferably, the tip 16 has a substantially smaller interior diameter than that of the reagent holding portion.

Figure 2:
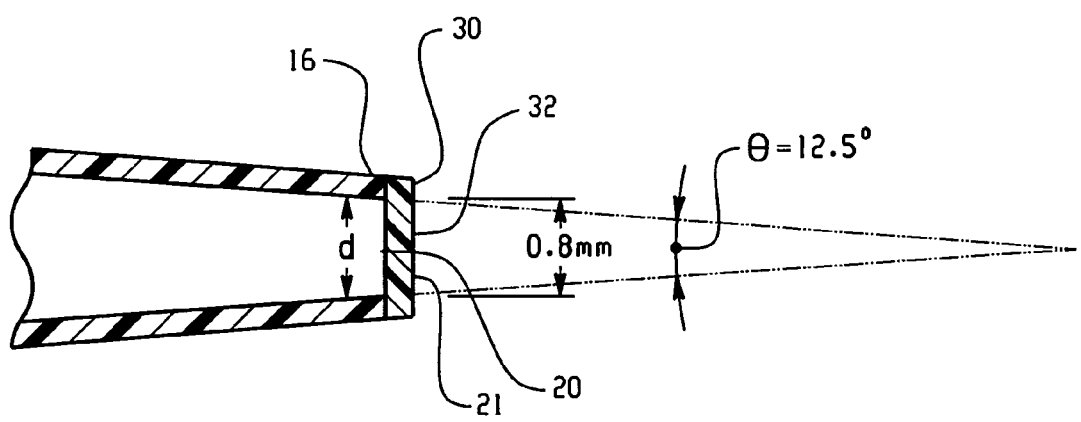
FIG. 2 is an enlarged side sectional view of the tip of the delivery device of FIG. 1.

In the embodiment of FIGS. 1 and 2, the tip 16 has the general shape of a bullet, which is conical with a delivery port 20 in the form of a small hole or holes at the end 21 of the tip, or near the tip end. The tip can be thus be a tapered portion of the body, which narrows between the reagent holding portion 13 and the delivery port 20. Alternatively, the tip has a cylindrical shape or other suitable shape. The size of the port 20 can be from about 10 microns to about 10 mm in cross sectional diameter, depending, in part, on the desired delivery rate, although larger or smaller dimensions are also contemplated. In one embodiment, the port 20 is from 10 to about 500 microns in interior diameter.

Figure 4:
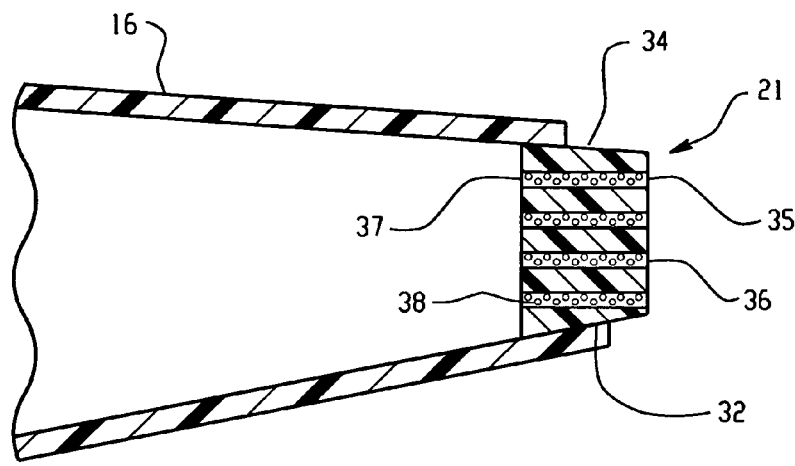
FIG. 4 is an enlarged side sectional view of the tip of a burette according to a third embodiment of a delivery device according to the present invention.

In the embodiment of FIG. 2, the delivery port 20 extends perpendicular to the longitudinal axis x of the body. It is also contemplated that the delivery port may be angled to the longitudinal axis x of the body, as shown in FIG. 4. This helps to reduce any tendency for air bubbles to become trapped in or around the delivery port.

In the embodiment of FIG. 1, the reagent holding portion 13 holds a filling comprising the reagent, optionally a solvent in which the reagent is dispersed to form a reagent solution 11, and optionally a matrix material 22, through which the reagent and solvent are able to permeate. This ensures that there is substantially no convection inside the burette. The matrix material is a solid or "semi-solid", such as a gel or a porous material (e.g., porous metals, such as inert metals e.g., nickel, titanium, and stainless steel, inert porous non-metallic materials, such as ceramic and glass, fibrous materials, such as fibrous glass, and combinations thereof) that contains the reagent solution 11. Suitable gels include agarose, polyacrylamide, other hydrogels, hydroxyethyl methacrylate (HEMA), and the like. The matrix material is preferably electrically neutral, and of low enough density to allow the reagent to permeate therethrough.

To avoid interactions with the reagent, the matrix material is preferably chemically inert towards the reagent. In one embodiment, the matrix material comprises a gel having a permeability which can be modulated via an electric voltage, voltage gradient, or other imposed electrical property. The delivery rate can thus be varied from external to the burette by a voltage controller or the like (not shown).

The gel helps to retain the reagent solution 11 within the burette until the tip of the burette makes contact with the target liquid. The gel allows the reagent to permeate therethrough.

The reagent is preferably in the form of a solution 11, such as an aqueous solution or non-aqueous solution. The reagent may be intimately mixed with and/or absorbed by the matrix material 22. Alternatively, or additionally, the matrix material is disposed between the reagent solution and the delivery port, as discussed in greater detail below. In an alternative embodiment, the matrix material is omitted.

The concentration of the reagent in the solution 11 depends, in part, on the desired concentration or concentration range of solutions to be prepared with the reagent. The concentration of the reagent can also be varied, dependent on the desired delivery time. Preferably, a plurality of burettes are provided, each one having a different concentration range, such that a user can select an appropriate burette according to the desired amount delivered, concentration, or concentration range. Alternatively, or additionally, other aspects of the burettes are modified to provide different absolute delivery rates and/or reagent, such as delivery port characteristics. For example, the target volume and desired concentration are first ascertained. From these values, the total amount to be delivered can be determined. The desired accuracy and precision of the delivered reagent and optionally the accuracy of tracking delivery time can also be taken into account in determining an optimum delivery rate. In some instances, such as in a titration or buffering in the target solution, the exact amount to be delivered is not known. In such instances, the amount delivered can be determined from the delivery time. Additionally, in some cases, the amount to be delivered cannot be determined from the volume of the target solution and the desired concentration. For example, where the reagent is undergoing a reaction as it is being delivered, such as in a titration, the desired delivered amount is dependent on the concentration of the corresponding reactant and/or the reaction end point. For example, the desired concentration of reactant in the target solution at the end point may be zero. Even though much larger amounts are actually delivered, the reactant is consumed. Similarly, where buffers are present, the amount delivered may be well in excess of what would be calculated from the final target concentration.

With reference now to FIGS. 2 and 4, a reagent permeable material 30 is optionally positioned in or adjacent the tip 16 of the burette, through which the reagent passes when leaving the burette. In this embodiment, the gel 22 may be omitted. As shown in FIG. 2, the permeable material 30 may be in the form of a porous membrane or layer 32, formed from cellulose, modified celluloses, such as acetyl cellulose or nitrocellulose, polyurethane, or the like. The membrane may be in the form of a single layer, as shown in FIG. 2, or multiple layers, as described in greater detail below. The membrane 32 may be about 2-100 microns in thickness, more preferably, less than 50 microns, most preferably, about 5-30 microns in thickness. FIG. 2 shows the membrane covering the tip end 21 and thus defining the delivery port 20, although it will be appreciated that the membrane may be positioned elsewhere in the tip 16 or shoulder 18 such that it provides a permeable member, which acts as a conduit, through which all of the delivered reagent diffuses from the burette.

In one embodiment, the membrane 32 is formed from a gel which has an electrically controllable property, such that the rate of diffusion can be controlled electrically, by an external device, as described above for the matrix material.

In yet another embodiment, the membrane 32 is formed from a material having holes in the form of pores 36, such as a thin layer of lipophilic or hydrophilic material, which may be 6-20 microns in thickness. The pores may be of micron or submicron diameter. For example, the pores may be from 0.01 to 100 microns in diameter. In one embodiment, the pores are at least about 0.1 microns in diameter. In one embodiment, the pores are less than about 10 microns in diameter. The pores 36 may be of uniform size or different sizes. An exemplary membrane material is a cyclopore membrane available from Whatman which has a clear and reproducible pore structure, although non-uniform pore sizes are also contemplated. Although having pores results in small semispherical volumes at the pore openings where concentrations are not uniform, the concentration at about 10-20 microns from the pores becomes substantially uniform due to the large number and small sizes of the pores. The pores thus produce a steady state delivery similar to a microelectrode array, with very little flow dependence on either side of the delivery port (flow in the target liquid or inside the burette body).

Specifically, the pores result in semispherical non-uniform volumes. This means that a local larger concentration exists at the center where the pore opening is located. A decaying concentration occurs along radial distance from the pore opening, so that local concentration depends on the distance from pore opening. If the semispherical concentration decays do not appreciably overlap, then the individual pores each deliver at steady state, which is independent of each other. If the pores are small enough, the pores produce small enough semispherical volumes that are too small for a modest flow to disturb, leading to constant delivery rate independent of small macro flows. The delivery rate is thus constant, after a negligible initial transient time during which the semispherical volumes form.

In another embodiment, shown in FIG. 4, the membrane 32 is from a rigid substrate 34 of a polymeric material, ceramic or the like, in the shape of a generally cylindrical body spanning the interior of the tip 16. The substrate 34 has a plurality of outlets 35, which together define the delivery port 20. Specifically, the substrate 34 is penetrated by a plurality of fine holes, such as bores 36 (FIG. 4) extending through the substrate between outlets 35 and inlets 37. The width of each of the bores 36 is dependent, to some extent, on the desired delivery rate and the method of forming the bores. For example, the bores 36 may in the general shape of hollow cylinders, although it is also contemplated that the bores may define convoluted paths or have different cross sectional shapes. The bore may be of about 0.1-300 microns in diameter. In one embodiment, the bores are about 10-200 microns in diameter. For example, the substrate 34 may contain 3, five, ten or more of such bores 36. In one embodiment there are from about 10-1000 bores. The bores 36 can be filled with a porous material 38 similar to that used for the matrix material 22 or membrane 32 in FIG. 2. As shown in FIG. 4, the membrane 32 is positioned at the tip end 21, although it is also to be appreciated that the substrate may be positioned elsewhere in the tip 16 and/or in the shoulder. It will be appreciated that the substrate 34 may be formed integrally with the tip 16 or be formed as a separate element, which is positioned in the tip.

In one embodiment, the bores 36 are all of the same width or of approximately the same width (e.g., at least about 90% of the bores are within ±20% of a median width of the bores, and can be within ±10% of a median width of the bores). In another embodiment, the bores are of different widths.

Figure 4A:
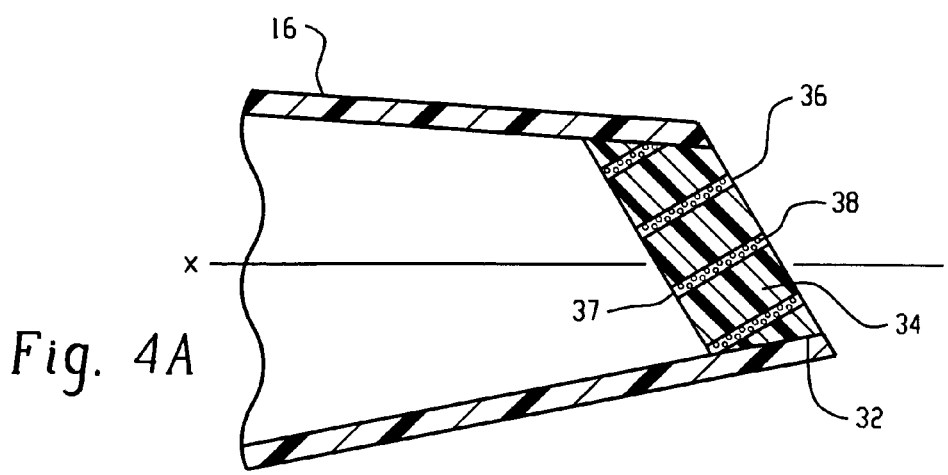
FIG. 4A is an enlarged side sectional view of an alternative embodiment of a tip of a burette according to a fourth embodiment of a delivery device according to the present invention.

In the embodiment of FIG. 2, the bores are aligned with the longitudinal axis of the body. It is also contemplated that the bores 36 may be angled to the longitudinal axis, particularly where the delivery port is angled to the longitudinal axis, as illustrated in FIG. 4a.

It will be appreciated that similar delivery rates can be achieved by reducing the number of bores and at the same time, increasing their diameter. For example, 10-30 bores of about 20-70 micrometers in diameter may yield a similar diffusion rate to about 3-8 bores of 100-200 micrometers in diameter.

To achieve bores 36 of suitable fineness, an Excimer laser may be used. The laser allows a single hole 36 or plurality of holes to be formed in a substrate 34 with a high degree of reproducibility—i.e., the bores are virtually identical. Making techniques can be used to define the locations of the holes to be drilled. In one embodiment, the laser is used to "drill" holes in a plastic or other polymeric material, such as a polyimide, (silicone) rubber, or polytetrafluoroethylene (Teflon™) material in the form of tubing or a sheet. The tube or sheet may be cut to the appropriate size for the substrate before or after drilling the holes. Excimer lasers are capable of forming bores of as little as about 10 microns in diameter, although bores of about 50 micrometers or greater are generally satisfactory.

Another method of forming holes 36 is to use silicon microfabrication technologies to produce the holes in a silicon or similar substrate 34. Such a substrate need not cover only the tip delivery port, it may be a large part or all of the burette body.

In one embodiment, the bores 36 are distributed in a ring, away from the center of the port. This allows for a more uniform and rapid dispersal of the reagent in the target solution, particularly when the tip is rotated, as is discussed below.

The burette 10 is intended to be disposable after use, although it is also contemplated that an empty burette may be refilled with reagent. In a preferred embodiment, large numbers of burettes are prepared by a supplier and shipped to facilities where the burettes are to be used. In one embodiment, each burette is used to prepare only a single target solution and is then disposed of.

The reagent is delivered from the burette into a target liquid by diffusion. This results in no or substantially no volume change in the target liquid during the addition of the reagent. By "substantially no volume change," it is meant that the target liquid does not increase or decrease in volume by more than 5% of the volume of the reagent solution 11 equivalent to the amount of reagent being transferred. More preferably, the volume change is no greater than 1% of the volume of the reagent solution equivalent to the amount of reagent being transferred. For example, if the reagent is in solution at a concentration of 1 Moles/L (1M) in the burette and it is desired to deliver 1 Moles of the reagent to the target liquid (i.e., the equivalent of 1 mL of reagent solution), the target liquid increases or decreases in volume by no more than about 0.05 mL, and preferably, by no more than 0.01 mL during the delivery time.

It will be appreciated that decreases in volume of the target solution can arise due to osmotic pressure. The high relative concentration inside burette causes water to flow into the burette due to the osmotic pressure difference. In general, the extent of water flow depends on the actual osmotic pressure difference between the target liquid 50 and the reagent solution 11 as well as on the characteristics of any membrane that separates the two. In practice, the effect of osmotic pressure upon target volume is negligibly small where the delivery time is in the minutes range, or less.

In one embodiment, the water (or other solvent) flowing between the burette and the target solution accounts for less than 10%, more preferably, less than 5%, and most preferably, less than about 1% of the equivalent volumetric delivery rate. The equivalent volumetric delivery rate F can be defined by the expression $$F = R/C_R$$

where R is the reagent delivery rate in moles per unit time and $C_R$ is the concentration of reagent inside the burette. F depends on the delivery port characteristics and the reagent concentration inside the burette.

For example, if the reagent delivery rate is 1 micromole/second and the reagent concentration in the burette is 1 M then the equivalent volumetric delivery rate would be 1 micromole/s per 1 mmole/mL=$10^{-3}$ mL/s=1 microL/s. Where delivery is achieved within a few minutes of operation, the effects of osmosis are negligible. Preferably, no more than about 10%, more preferably, less than 5%, most preferably, less than about 1% of this value will be water flow, i.e., in the example above, a volume change of less than 0.1 μL/second, more preferably, less than 0.05 μL/second, most preferably, less than 0.01 μL/second is due to water flow. In practice, the volume change due to water flow is typically in the direction from the target into the burette, and is typically far less than 5% of the equivalent volumetric delivery rate. In some cases, there is effectively no change in volume of the target solution, since the rate of reagent delivery from the burette to the target solution is approximately balanced by the water flow from the target solution to the burette.

To form the burette 10 of FIG. 1, the reagent solution 11 of choice is mixed with a gel forming material, such as agarose powder or other polymer forming material which is then loaded into to the chamber 14 and the gel allowed to set. The cap 17 is then screwed or otherwise attached to the open end 15 of the burette. The reagent remains within the burette, trapped by the gel until the tip 16 is placed in contact with the desired target solution.

Where a solid matrix material such as a porous ceramic is used, the porous material is immersed in or otherwise contacted with the liquid reagent solution 11. Vacuum infiltration techniques may alternatively be used to introduce the reagent solution to the porous material. The porous ceramic may be loaded into the chamber 14 prior to introduction of the reagent solution or loaded after introduction. Or, as described in greater detail below, the body 12 may be formed around the infiltrated porous material or gel/reagent solution mixture.

If no matrix material is used, the reagent solution 11 is introduced directly to the burette chamber. In this case, the membrane 32 is sufficiently resistant to the passage of the reagent solution therethrough that there is substantially no escape of the reagent from the body until it is able to move by diffusion into a target liquid in contact with the membrane. Where the matrix material and reagent solution are to be inserted separately, the matrix material can be added first and allowed to set before the reagent solution is introduced.

Figure 5:
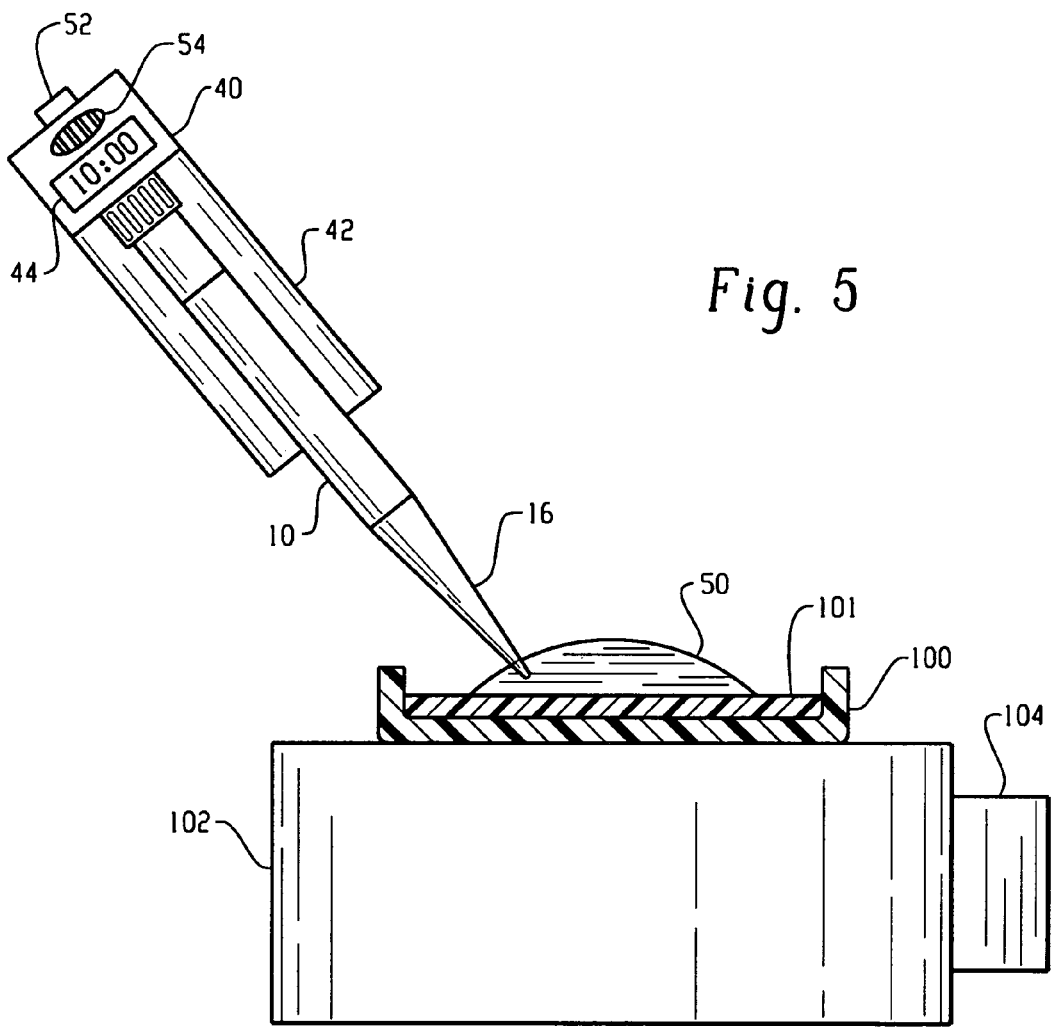
FIG. 5 is a side view of a delivery system including the delivery device of FIG. 1 with a dispensing device attached for delivery of a reagent into a target solution with a vibrator for mixing the target solution.

The burette 10 may be used immediately after formation or shipped and/or stored for a period of time prior to use. Accordingly, multiple burettes can be prepared and used as needed. The burette 10 holds the reagent solution until the tip is placed in fluid contact, generally in direct contact, with a target liquid 50 in which a target solution containing the reagent is to be formed (FIG. 5). Contact is maintained with the target liquid for a sufficient time (the delivery time) to form the target solution. This operation may be carried out manually, by an operator holding the burette and contacting the target liquid with the tip, or mechanically, as described in greater detail below.

In one embodiment, the burette 10 contains sufficient reagent to form a plurality of target solutions. It will be appreciated, however, that with each additional delivery, the concentration of the reagent in the burette tends to decrease, since the volume of solution in the burette remains essentially constant. Accordingly, the delivery time for second and subsequent deliveries is generally increased for forming corresponding target solutions of the same concentration and volume. The delivery time for a particular delivery in a sequence of such deliveries can be calculated, either empirically, or by using mathematical formulae, as will described in greater detail below.

Optionally, a dispensing device is provided for the burette 10. In one embodiment, shown in FIGS. 3 and 5, a dispensing device 40 selectively holds a burette in a sleeve 42 or other receptacle. A fresh burette 10 is inserted into the sleeve and a timing device, such as a clock 44 is reset to zero or to a desired delivery time, e.g., 10 seconds. The resetting of the clock may be carried out automatically by the burette pressing on a reset button 46 during insertion into the sleeve.

When the burette 10 is to be used to form a target solution, the tip 16 is placed in the target liquid 50 into which the reagent is to be delivered (FIG. 5) and the user simultaneously presses a button 52 on the dispensing device to start the clock 44. The reagent flows through the membrane into the target liquid. When the clock indicates that the desired delivery time has elapsed, the user removes the burette 10 from the solution, halting the reagent flow. Alternatively, or additionally, an alarm 54, such as a buzzer or flashing light, indicates when a desired delivery time has elapsed to alert the user to remove the burette tip 16 from the target solution. When the burette 10 is depleted, it is removed from the dispensing device 40 and the dispensing device can be reused with a fresh burette.

Figure 6:
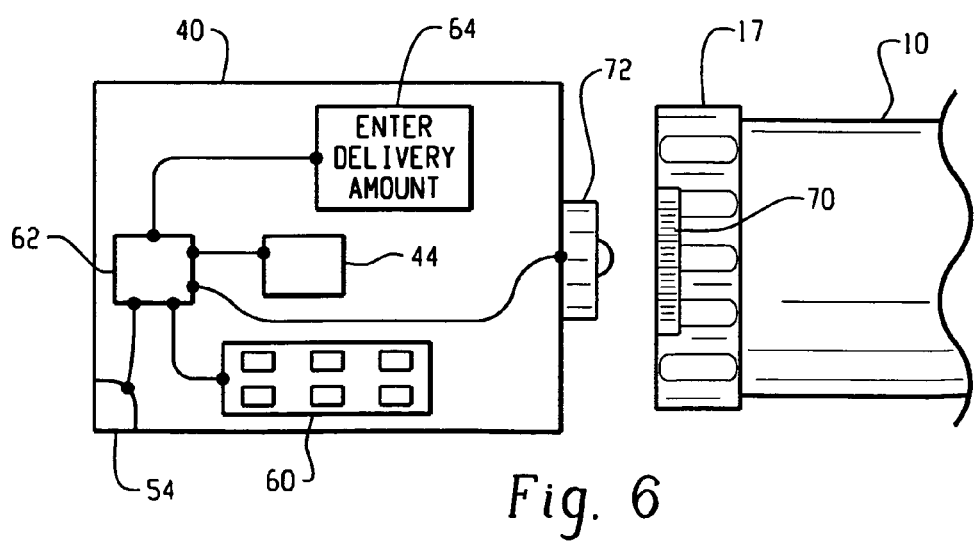
FIG. 6 is an enlarged view of an alternative embodiment of a dispensing device adjacent a cap of a burette having a barcode thereon.

In one embodiment, shown in FIG. 6, the user uses a keypad 60 or other input device to instruct the timer device or a control system, such as a microprocessor controller 62 associated with the timer device 44 how much reagent is to be delivered. The control system is programmed with information concerning the delivery rate of the reagent from the burette 10 and other factors affecting delivery, such as the amount of reagent which has already been delivered from the device. The control system 62 determines how long it will take to deliver the desired amount of reagent and sets the clock 44 accordingly. In one embodiment, the control system interrogates the user by means of a screen 64 and the user inputs information which affects the delivery rate, e.g., via the keypad 60. For example, the control system 62 may ask the user for the concentration of the reagent in the burette being used, or for information regarding one or more of the ambient temperature, the desired delivery amount, the target concentration and the volume of the target solution. The control system uses this information in determining the appropriate delivery time. The control system may also ask the user for the desired final accuracy and precision. Based on the input values, the control system recommends a particular burette to be used (i.e., one that has low enough delivery rate such that the total delivery time is long enough to be controlled precisely and accurately.

To accommodate the demands of a variety of consumers, it is contemplated that a series of burettes of different dimensions, sizes, shapes, and material are provided to accommodate different reagents, concentrations, delivery rates, and the like. Identifying information, such as reagent type, concentration, volume, and the like, e.g., in the form of a computer recognizable indicia, such as a bar code 70, may be provided for each burette 10. The bar code is preferably affixed to the burette 10 or to packaging associated therewith. The bar code may also provide other information, such as the date of fabrication and filling, delivery rate, information for programming a timer device, and the like. Other recognition information may be provided, so that a user may keep track of the amount of reagent that had been delivered from a particular burette, allowing an adjustment of the calibration to be automatically made, if appropriate.

Figure 7:
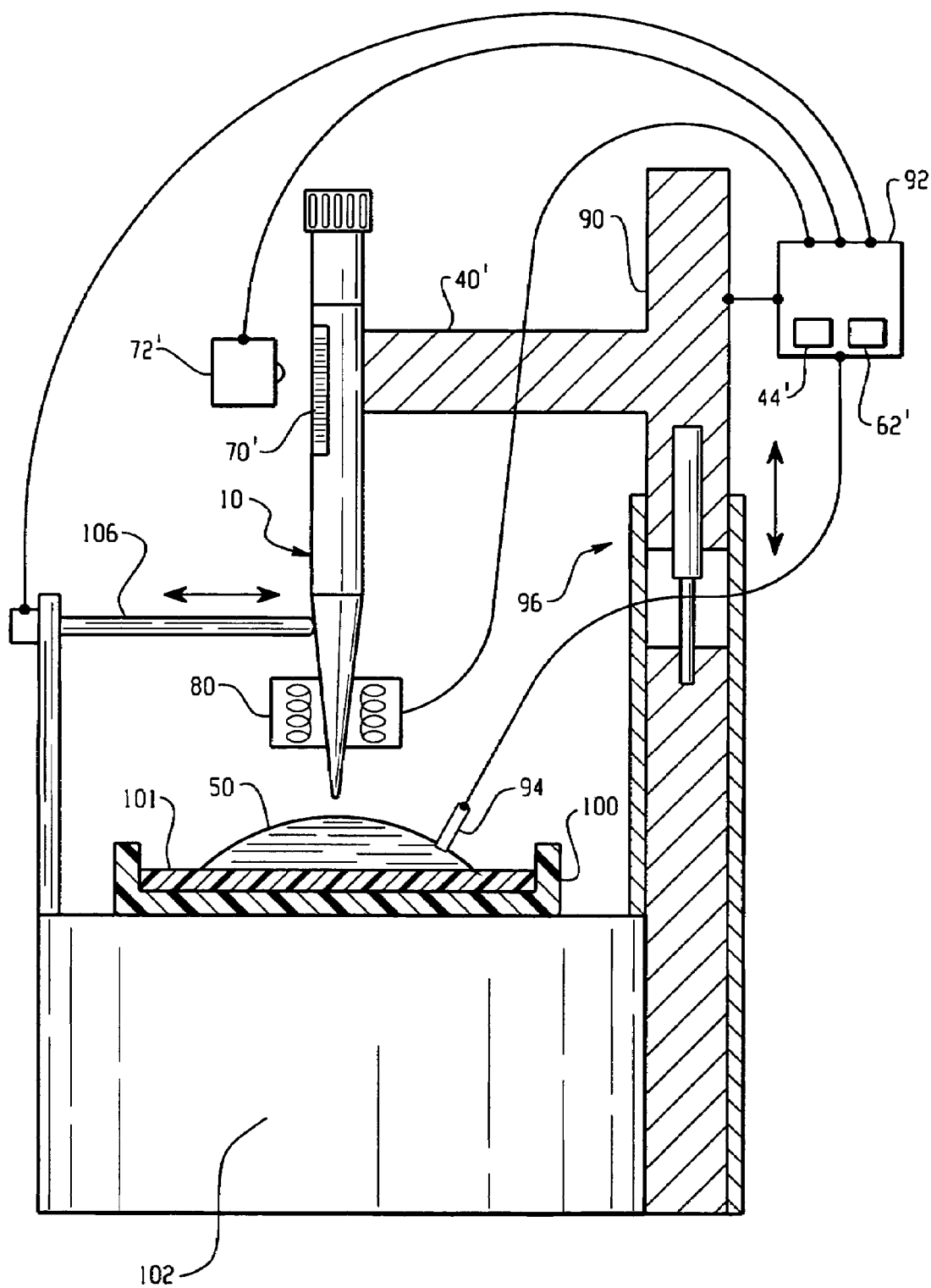
FIG. 7 is a side view of an alternative embodiment of a delivery system including a stand for lowering a burette, an agitation means for vibrating the burette tip, and a support for a container of a target solution.
Figure 16:
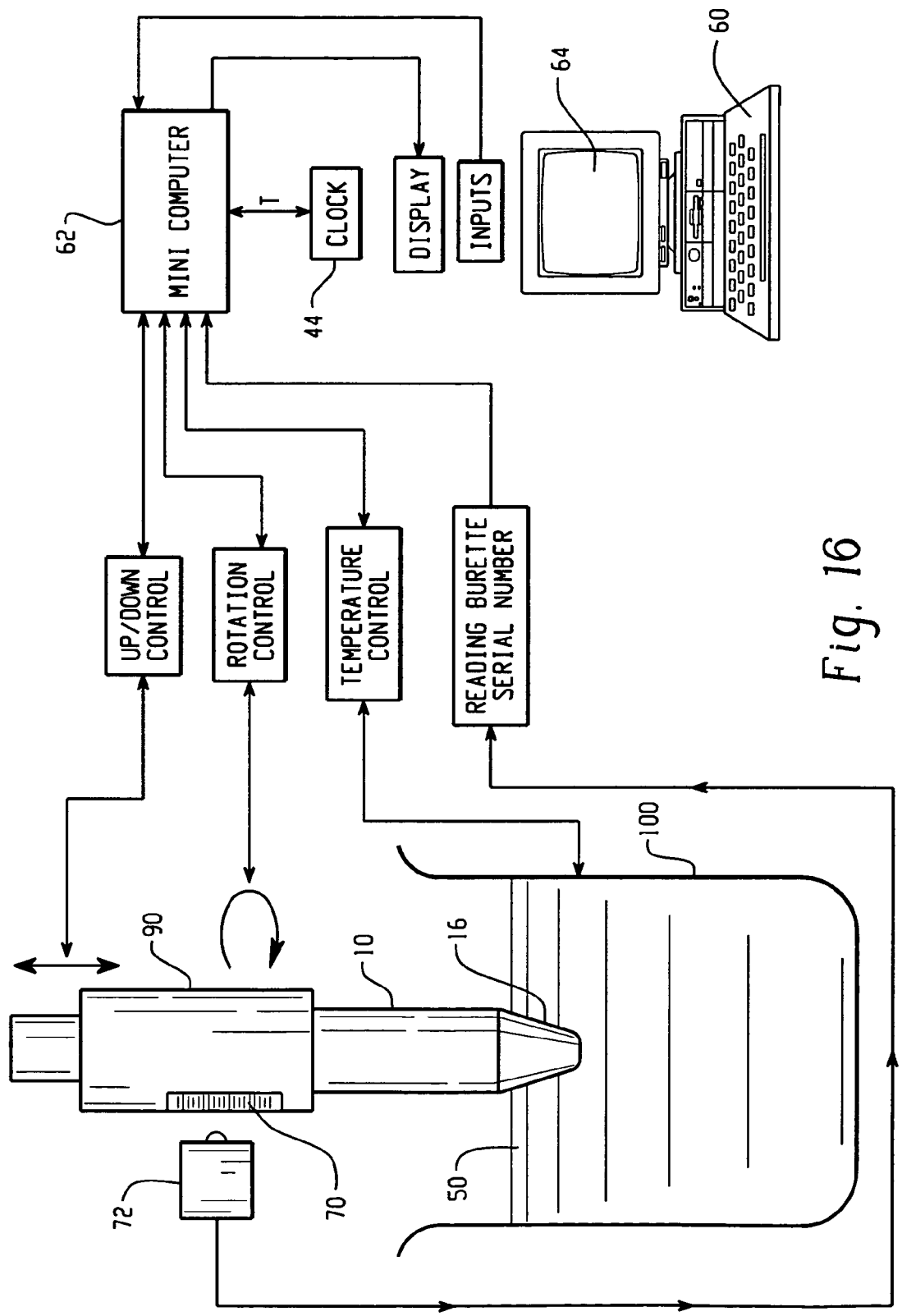
FIG. 16 is a schematic view of a processor controlled delivery system according to another embodiment of the present invention.

In one embodiment, shown in FIGS. 6, 7, and 16, the control system 62 is programmed to recognize the bar code 70 using a bar code reader 72. The control system optionally informs the user about the particular burette or makes calculations based on stored information about the burette which corresponds to the bar code. The bar code may be printed on an inside surface of the burette, to protect the bar code or some other condensed digital code system from outside dirt or contamination or obscuring effects or to ensure confidentiality of the information. The control system may also display, for example, which one of the different burettes of identical type should be used for delivering a given amount with a given precision. This is because the longer the delivery time (i.e., the slower the delivery rate), the higher the relative precision of the total amount delivered. The control system may include look-up tables, algorithms, or the like from which it calculates a desired delivery time, delivery rate, or the like, based on information scanned from the bar code 70 and/or or operator input information.

Figure 3:
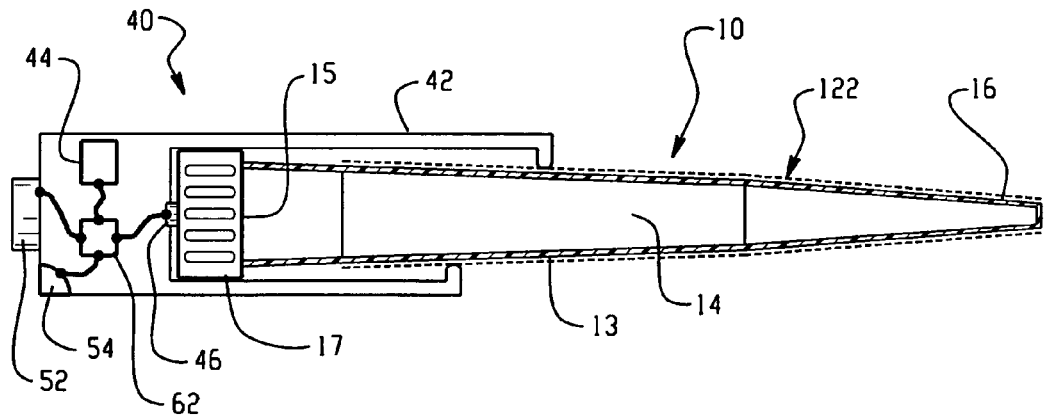
FIG. 3 is a schematic side sectional view of a second embodiment of a delivery device according to the present invention.

In place of a dispensing device 40, with its own clock 44, as shown in FIG. 3, a stopwatch or other timing device 44 is alternatively used by the user to monitor the delivery time.

Diffusion rates depend, to some degree, on ambient temperature. Accordingly, particularly when extremely precise quantities are to be delivered, controlling the temperature and/or correcting for temperature helps to ensure accuracy. Thus, in one embodiment, a controlled temperature environment (such as is generally provided in wet chemistry laboratories) is employed for deliveries from the burette 10. Both the burette 10 and the target liquid 50 in to which the delivery is to be made are allowed to equilibrate in the controlled temperature environment prior to delivery. Alternatively, for example, where a controlled environment is unavailable, the target liquid and/or burette are brought to a preselected temperature (e.g., by heating or cooling) prior to delivering reagent from the burette. In yet another alternative embodiment, corrections are made to the delivery time depending on the detected ambient temperature. The effect of small temperature variations on the delivery characteristics is estimated by using physicochemical theory, or from prior empirical measurements.

FIG. 7 illustrates a dispensing device 40', where similar components to dispensing system 40 are labeled with a prime (') and new elements are given new numbers. In the embodiment of FIG. 7, a heating element 80, such as a resistance heater, provides local heating of the tip 16 and optionally all or part of the reagent holding portion to heat the reagent solution therein. This allows thermostatic control of the delivered reagent (and thus, the temperature of the delivery diffusion process) and hence a more reproducible delivery rate, particularly where ambient temperatures are prone to fluctuation. The heating element 80 may also provide different heating levels, making the delivery rate tunable. This can be used to increase or decrease the delivery rate (increasing the temperature increasing the delivery rate, decreasing the temperature decreasing the delivery rate).

In one embodiment, the heating element heats the entire delivery port and membrane and optionally also an adjacent portion of the target liquid 50. This ensures that those elements whose temperature may affect delivery rate to some degree are at the same, reproducible temperature. For example, a partial casing or screening of a volume fraction of the target liquid closest to the delivery port is effected to ensure that the volume fraction whose temp may have an effect on the resulting effective delivery rate is effectively thermostatted. The remainder of the target liquid may then be at a slightly different temperature, without there being a significant influence on the delivery rate.

It has been found that an approximately 10° C. increase in temperature may result in a doubling in the rate of a number of physicochemical processes, such as diffusion rate. A heating element 80 at or near the tip 16 of the burette 10 thus allows a constant temperature, which is higher than ambient, during the delivery by heating it above the ambient temperature. Additionally, heating enables the user to achieve different delivery rates using temperature modulation of the diffusion rate. It is also contemplated that a constant temperature may be achieved by cooling the tip. If a very small volume is to be cooled (or heated) then this can be effectively achieved using a heating or cooling element 80 employing conventional technologies (for example, for cooling, an electronic cooling system or heat pump can be used).

The delivery from the burette 10 into a target liquid 50 is continuous, with a rate which can generally be as low as practically desired. For intermittent additions, such as multiple standard additions, the burette tip 16 is removed from the target liquid and returned to the target liquid for each addition. For introducing the tip to a target liquid, a support means, such as a stand 90 is optionally used to lower the tip 16, either manually or by an automated operating system 92 into the solution, as illustrated in FIG. 7. The automated system includes a processor 62' analogous to processor 62. An automatic sensing device 94, electrically linked to the operating system 92, optionally senses the time when the tip first contacts the solution. The automated sensor 94 may use electrical impedance for detecting contact. The timing mechanism 44' starts counting the time from that moment. At the end of the preselected delivery period, the operating system 92 withdraws the tip from the target solution. In one embodiment, the stand 90 includes a mechanical lifting device 96, such as a piston operated actuator, e.g., operated by a motor (not shown) for removing and inserting the tip 16 into the target liquid 50 by lifting/lowering the burette 10. The mechanical lifting device 96 can be controlled by processor 62' to remove the tip 16 from the target liquid when a desired delivery time has elapsed.

As shown in the embodiment of FIGS. 5 and 7, the target liquid 50 is preferably placed in a suitable container 100. The container is optionally formed from or lined with a containment layer 101 such as a silicone layer, for creating surface tension forces which contain the target liquid on as small area of the containment layer as an approximately hemispherical bead of liquid. Where the reagent solution is hydrophilic, containment layer 101 is preferably formed from a hydrophobic material, and vice versa. The container 100 is optionally positioned on a support 102. Optionally, a means for stirring the target liquid 50 or reagent is provided. In the embodiment of FIG. 5, the support 102, and hence the container 100 and target liquid 50, is vibrated by an agitator in the form of a vibrator 104, although other suitable stirring means are also contemplated, such as fine gas jets or bubbling or integrated MEMS devices. The vibrator stirs the target liquid, helping to maintain the homogeneity of the target solution as the reagent is added.

In another embodiment, illustrated in FIG. 7, the reagent in the burette is stirred. In this embodiment, the means for stirring includes an agitator, such as a vibrator or rotator 106, which causes the tip 16 or other portion of the burette 10 to vibrate, rotate or otherwise move. The vibration/rotation or other movement of the tip 16 stirs the reagent solution in the burette 10, maintaining its homogeneity in the burette as reagent is dispensed. The agitator 106 also causes the tip 16 to stir the target liquid 50, when the tip is placed in contact therewith. It will be appreciated that more than one means for stirring 104, 106 may be employed, either during or subsequent to a delivery. The stirring means 104, 106 is preferably under the control of the operating system 92.

The rotation of the burette 10 (or other form of agitation) results in an adjustable enhancement of the delivery rate (i.e., allows for reductions in the delivery time) and tends to reduce errors which may arise from unwanted spontaneous convection.

Figure 8:
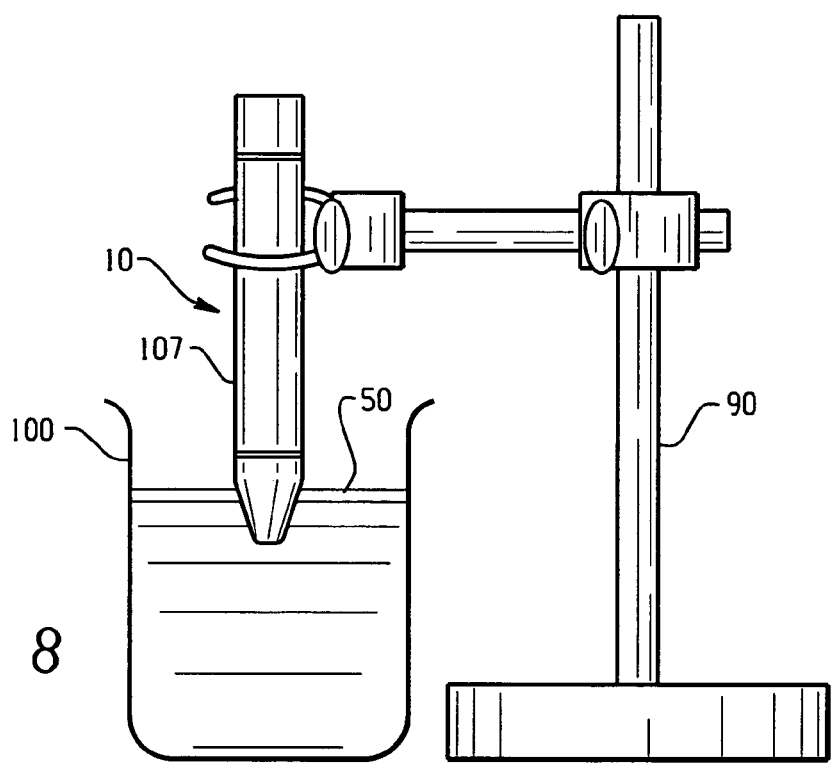
FIG. 8 is a perspective view of a fifth alternative embodiment of a delivery device according to the present invention, supported on a stand with a tip of the delivery device positioned in a target liquid.
Figure 9:
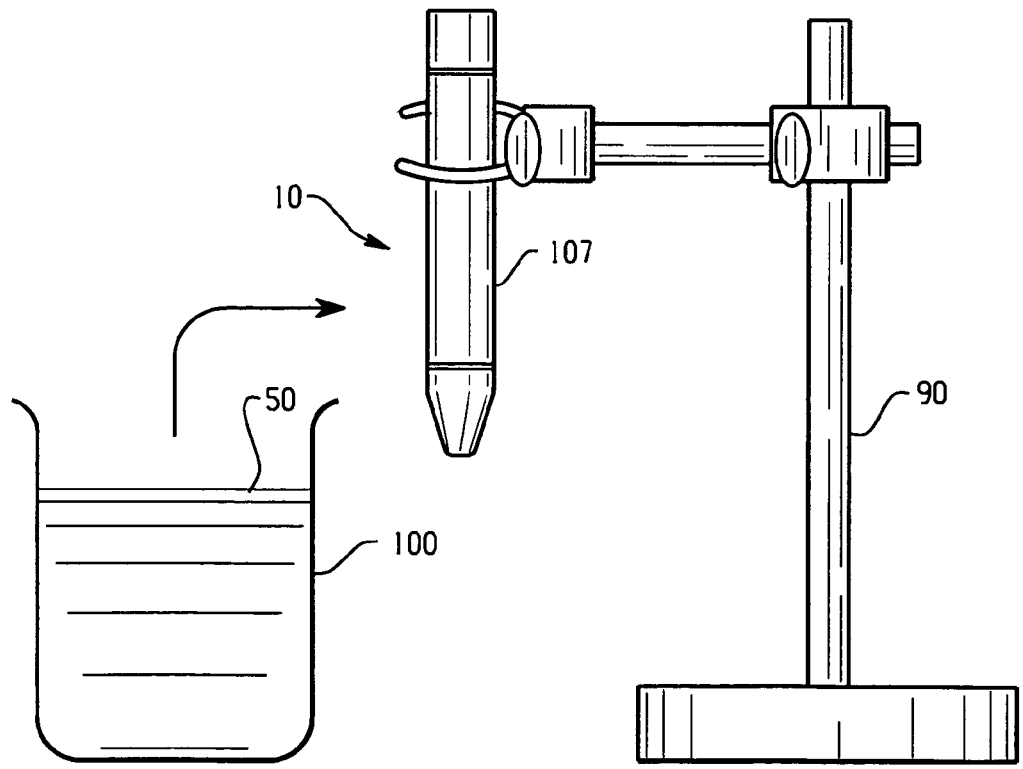
FIG. 9 is a perspective view of the delivery device of FIG. 8, supported on a stand, after removing the tip from the formed target solution.
Figure 10:
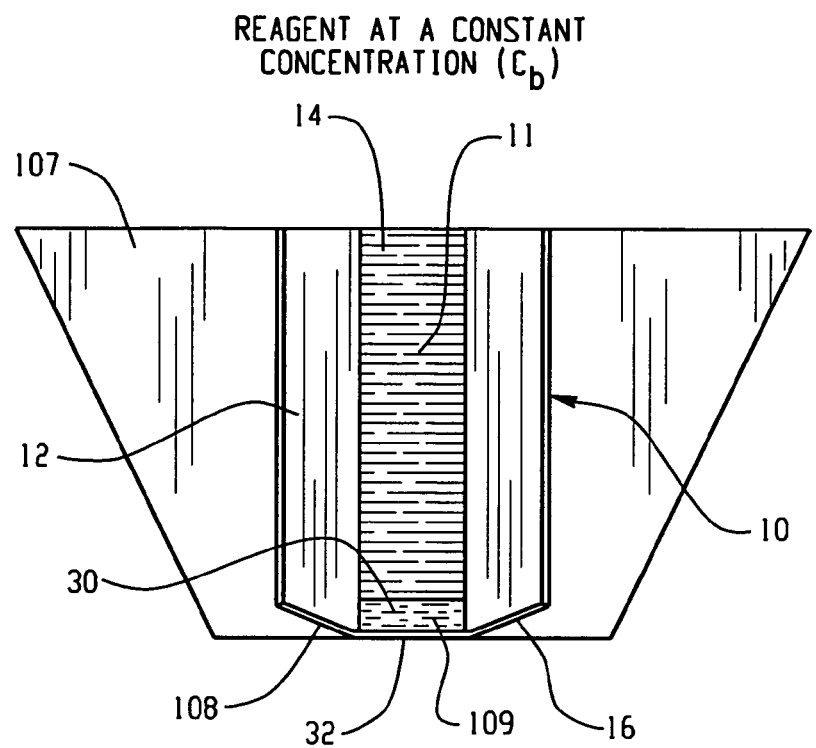
FIG. 10 is an enlarged sectional view of the tip of the delivery device of FIG. 8.
Figure 11:
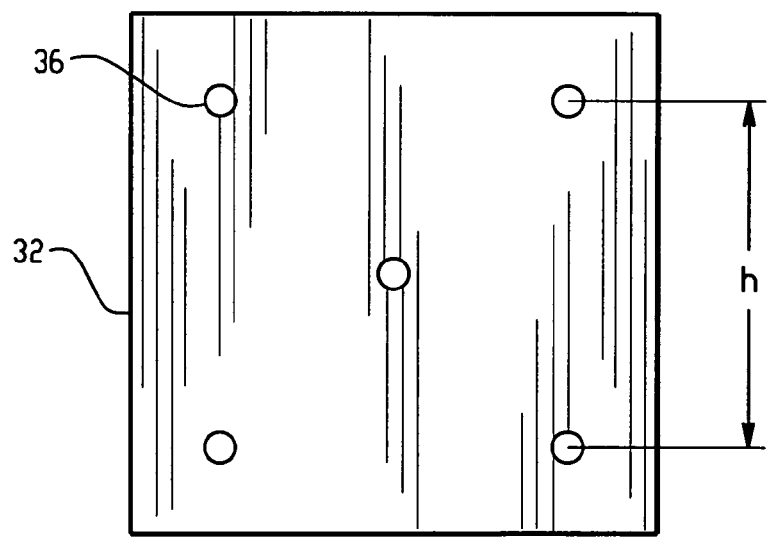
FIG. 11 is an enlarged top view of the membrane of the delivery device of FIG. 8.

With reference now to FIGS. 8-11, a burette 10 similar to that shown in FIGS. 1 and 2 is shown. For convenience, similar elements are given the same numbers and new elements are given new numbers. The burette includes a housing 107, formed from plastic, or other suitable material which surrounds the body 12 and has an opening 108 at a lower end, through which the delivery port 20 is exposed (FIG. 10). The body is formed from an inert material, such as polyacetal resin, Teflon®, or the like and holds a quantity of a reagent solution 11. A reagent permeable material 30 in the form of a membrane 32 closes the delivery port 20 and is permeable to the reagent. In one embodiment, reagent permeable material also includes a layer 109 formed from a matrix material, such as a gel, e.g., an agar gel or other material allows the reagent to pass therethrough by diffusion, although it is also contemplated that the gel may be mixed with the reagent solution, as shown in FIGS. 1-4. The membrane layer 32 can be formed from a substrate, such as a polyimide or other plastic material or an inert metal sheet or other inert membrane material which is impermeable to the reagent, except where holes 36 are provided. The membrane may be, for example, about 20-30 microns in thickness. As shown in FIG. 11, the membrane 32 has a plurality of holes 36 (five in the illustrated embodiment), through which the reagent passes. The holes may be about 10-100 microns in diameter, e.g., about 50 microns in diameter, or other suitable widths, as noted above, and may be a distance h of about 0.01 mm to about 2 mm apart. The many holes (bores- or pores in the case of a cyclopore membrane) are ideally as close to each other as possible (to reduce overall size) without causing the resulting semispherical nonuniform concentration domains to overlap. The remainder of the polyimide film 32 is impermeable to the reagent, such that the reagent diffuses from the burette via the holes. The holes 36 may be formed by drilling bores, e.g., with a laser, as described above. Or the membrane layer 32 can be formed with pores.

Figure 12:
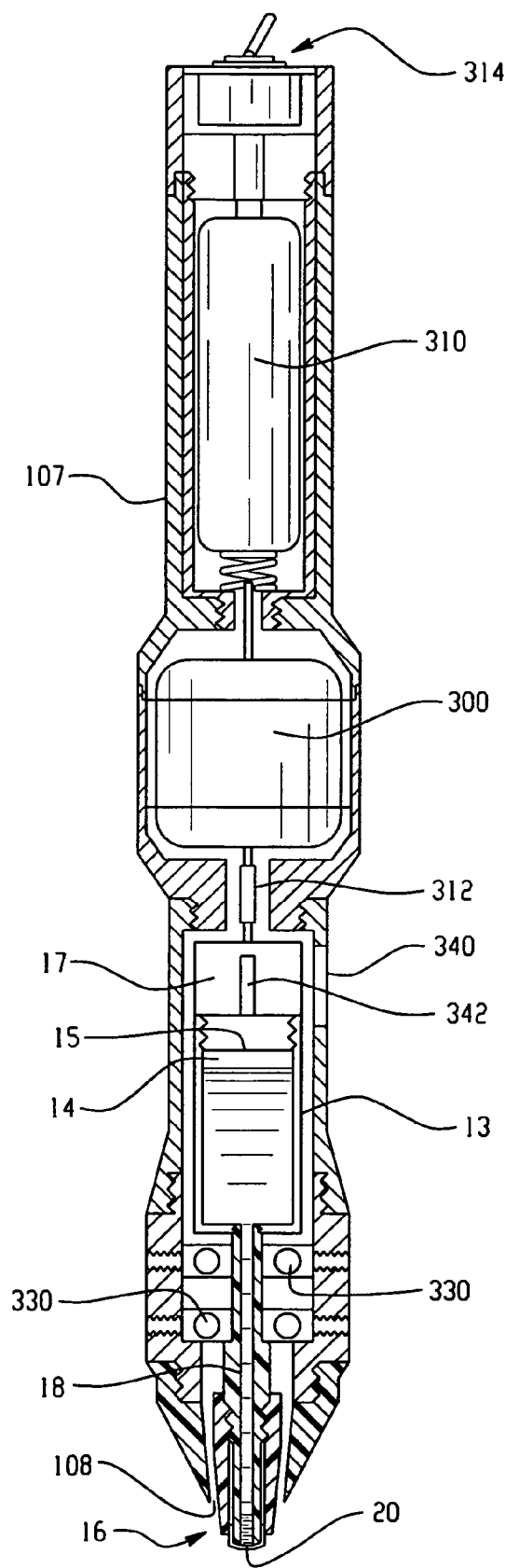
FIG. 12 is a side sectional view of a sixth alternative embodiment of a delivery device according to the present invention, with a tip of the delivery device undergoing rotation.

In one embodiment, illustrated in FIG. 12, a burette 10 similar to that of FIGS. 8-11 includes a tip 16 which is rotatable. The burette includes a housing 107, formed from plastic, or other suitable material, which surrounds the body 12 and has an opening 108 at a lower end, through which the delivery port 20 is exposed. The housing holds the burette body 12 and a motor 300 powered by a power source, such as a battery 310, which in the illustrated embodiment is mounted within the housing, above the motor 300, although other locations are also contemplated. Alternatively, a remote source of power, such as mains supply, is used to power the motor and is connected thereto by suitable electrical wiring.

The motor 300 is connected by a drive shaft 312 to the cap 17 of the burette and thus imparts rotational movement to the body 12 of the burette. A switch 314, mounted to the housing, controls the motor. The switch may be a simple ON/OFF switch, or it may be a variable switch, which allows the speed of the motor to be varied. The motor may rotate the body at a speed of from about 50 to about 20,000 rpm. In one embodiment, the motor rotates the body at from about 1000 to about 5000 rpm.

Figure 12A:
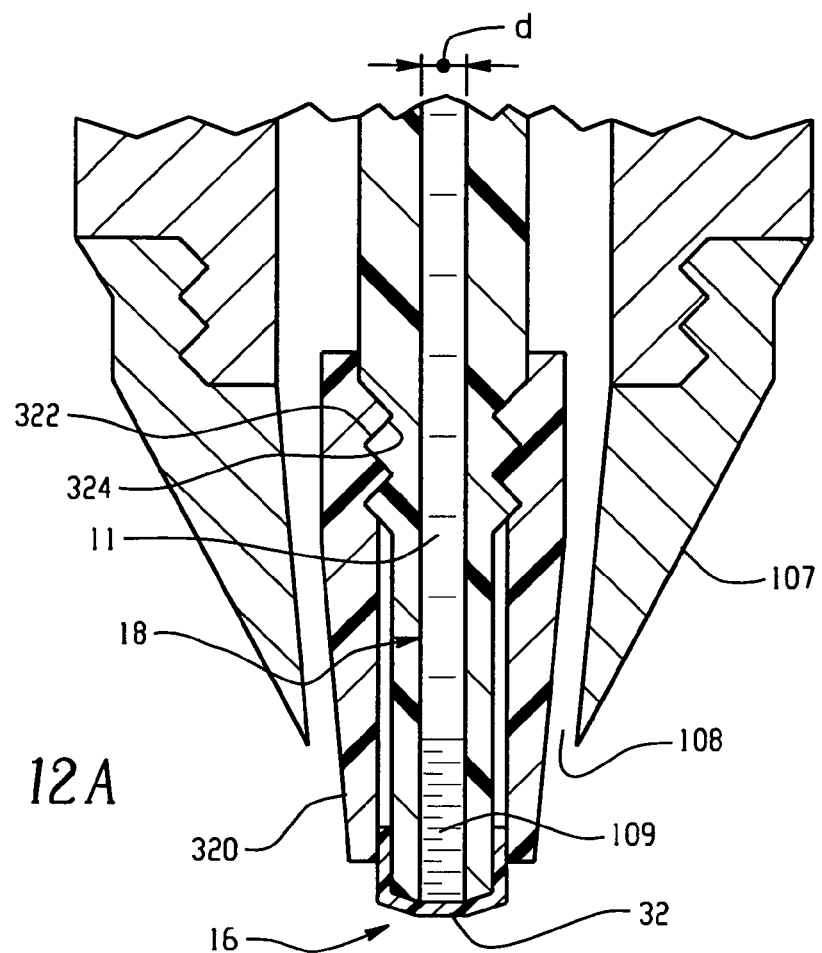
FIG. 12A is an enlarged side sectional view of the tip of the embodiment of FIG. 12.
Figure 12B:
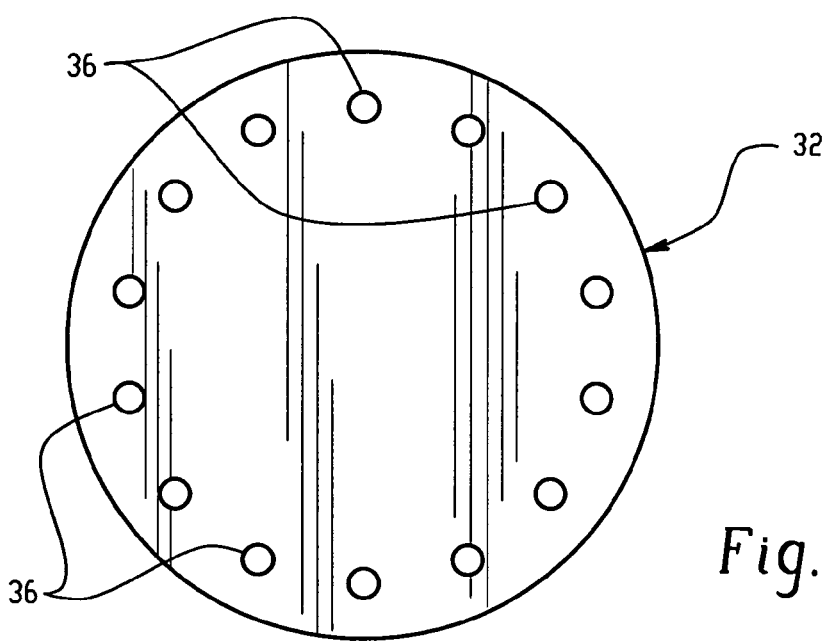
FIG. 12B is an enlarged bottom view of the membrane of the embodiment of FIG. 12.

The body 12 includes a reagent holding portion 13, which defines an interior chamber 14 that holds a quantity of a reagent in solution 11, which is introduced to the chamber via an opening 15 at one end of the chamber 14. For example, the chamber may hold about 5 mL of reagent solution 11. The body also includes a tip portion 16, in fluid communication with the other end of the chamber 14, through which the reagent is delivered from the burette. FIG. 12A shows the tip in greater detail. Intermediate the tip portion 16 and the reagent holding portion 13 is a tubular portion 18. The tubular portion has an internal diameter which is generally constant from the tip to the reagent holding portion, although conical or other shapes are also contemplated. The internal diameter d of the tip, which in this embodiment, also corresponds to the diameter of the tubular portion 18, can be as for other embodiments of the burette. In one embodiment, the diameter d is about 5 mm. A membrane 32 covers the delivery port. The membrane can be as previously described, e.g., of about 10-50 microns in thickness and have a plurality of bores drilled therethrough or otherwise formed therein, similar to those illustrated in FIG. 4, or be a naturally porous material. The bores/pores provide a plurality of through passages between the interior of the body and the exterior. As shown in FIG. 12B, the bores 36 are located in a ring, spaced from the axial center of the membrane 32 and preferably closer to the exterior of the membrane than to the center of the membrane. In this way, the reagent is carried away from the tip 16 by the fluid flow pattern in the target liquid 50, induced by the rotation of the tip in the target liquid. Closer to the axial center of the tip, the flow pattern tends to result in a lower flow rate.

The membrane 32 is carried by a membrane fitting 320, which is shaped to connect with the tube 18. Specifically, the membrane fitting is internally threaded at 322 and engages corresponding threads 324 on an exterior of the tube 18. In this way, the membrane 32 can be removed and replaced if desired. The membrane is optionally in direct contact with a gel layer 109 as described for the embodiment of FIG. 11.

As illustrated in FIG. 12, ball bearings 330 or other suitable guide members are located within the housing 107, close to the tip 16 of the burette for guiding the tube 18 during rotation of the burette.

As shown in FIG. 12, the housing 117 may have a window 340, which provides access for a non-contact tachometer (not shown) or other means of measuring the rotational speed of the burette. An optical reflector 342, or other detectable strip is mounted to a rotating portion of the burette, such as on the cap 17, as illustrated. The tachometer is thus able to determine the speed of rotation of the burette from the number of times the strip passes the window in a given period. The detected rotational speed can be fed to a controller which adjusts the rotational speed of the burette, for example, by increasing the power supplied to the motor, in accordance with predetermined set rotational speed values.

Figure 13:
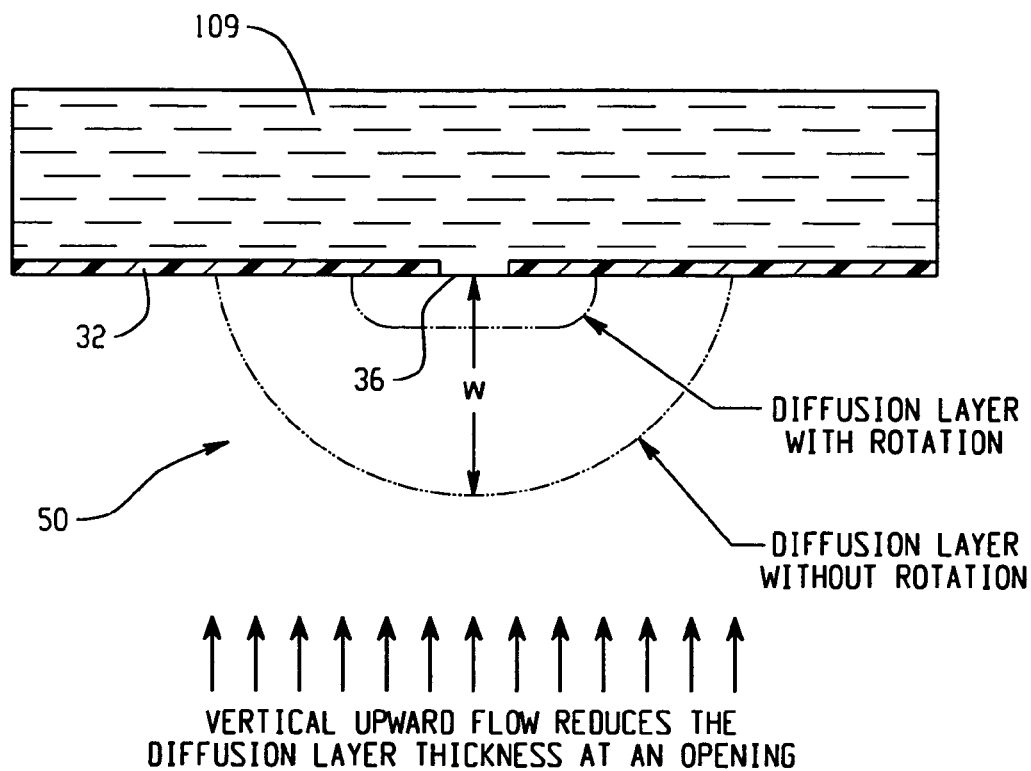
FIG. 13 is an enlarged sectional view of the membrane of the delivery device of FIG. 12, illustrating the diffusion layer in a target liquid around a hole in the membrane, both with and without stirring, showing that the diffusion layer is reduced in thickness when stirring is used.

FIG. 13 shows the diffusion layer of width w surrounding one of the holes 36 in the membrane 32 of the device of FIGS. 10-12 during delivery of a reagent to a target liquid 50. The limit of the diffusion layer with and without rotation of the tip is shown. As can be seen, rotation of the tip reduces the thickness of the diffusion layer by at least 50%, and typically by at least 70%.

It will be appreciated that the burettes shown in FIGS. 8-12 can incorporate other features of the burettes shown elsewhere, such as heaters, control systems, timing devices, and the like.

FIGS. 8 and 9 show the burette 10 supported on a stand 90 for raising and lowering the burette. As will be appreciated, the device of any of the FIGURES shown herein can be similarly mounted on a stand. However it will be appreciated that a burette 10 can be introduced manually to the target liquid 50, as in the embodiment illustrated in FIGS. 5, 14 and 15. A pen-type burette 10 illustrated in FIGS. 14 and 15 includes a housing 107, which surrounds the body 12 (not shown). During delivery, the tip 16 of the body protrudes though a suitably sized aperture 108 in the housing. After delivery, the tip is retracted back into the housing. The movement of the tip into and out of the housing is controlled by a start button 52 on top of the housing, which also starts and stops delivery. For example, to start delivery the tip is pushed out to contact the target solution and to stop delivery, the tip is pulled back into the housing so that contact between delivery ports and target solution ceases. The tip 16 preferably includes a membrane 32 (not shown) similar to that illustrated in FIGS. 2, 4, 4a, 10, or 12.

Figure 14:
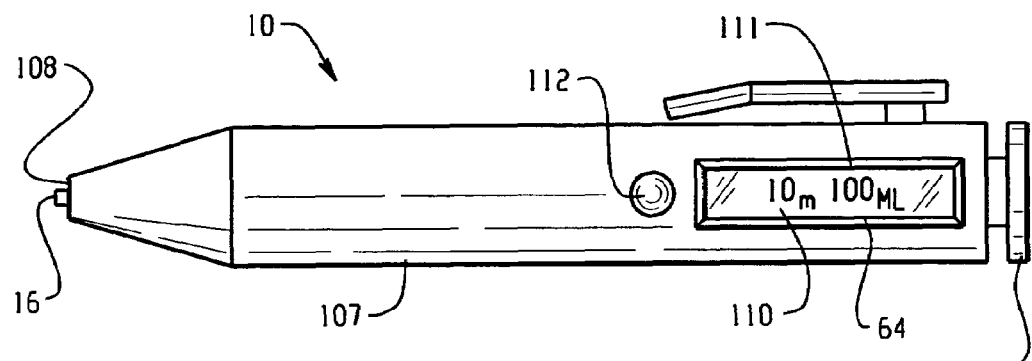
FIG. 14 is a perspective view of a pen-type delivery device according to a seventh embodiment of the present invention.
Figure 15:
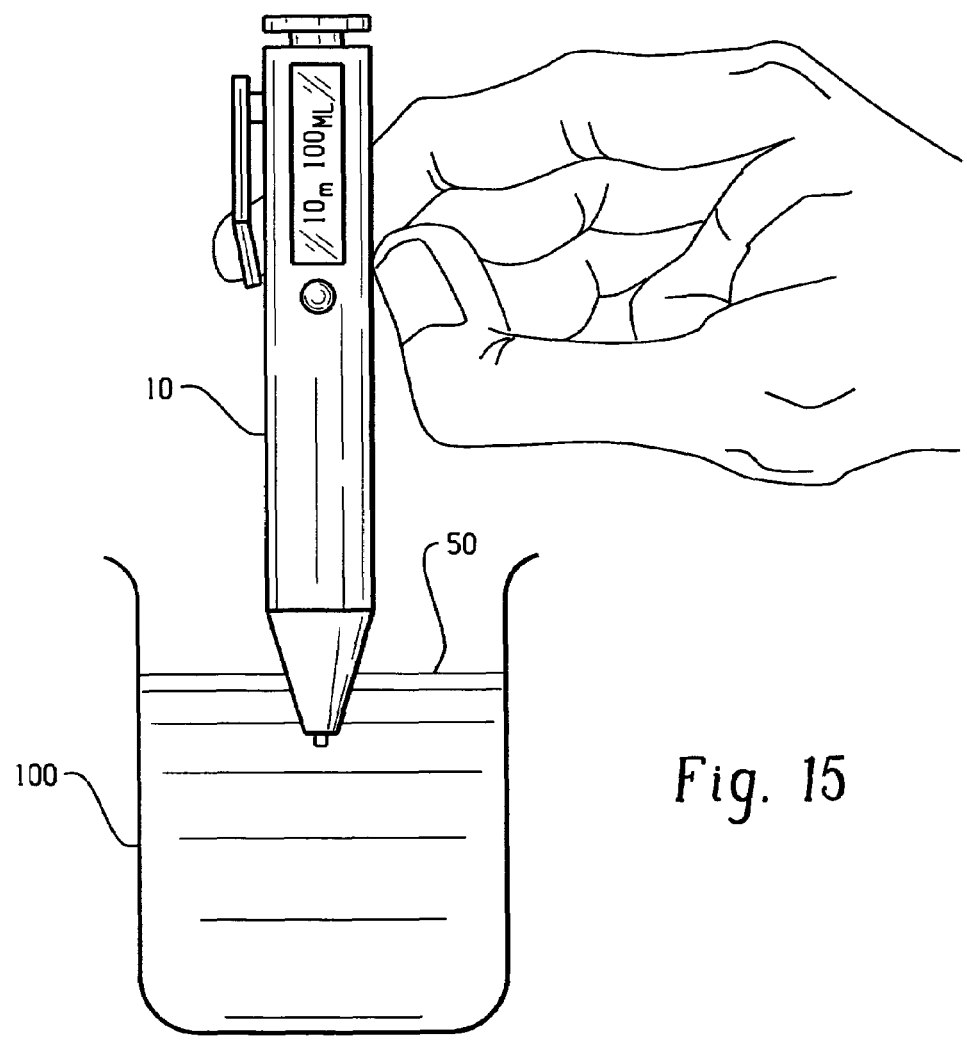
FIG. 15 is a perspective view of the pen-type delivery device of FIG. 14, being manually inserted into a target liquid.

With particular reference to FIG. 14, a window 110 in the housing 107 is covered with a transparent material through which a display screen 111 is visible. The display screen 111 provides information on the volume of the target liquid (10 mL in the illustrated embodiment), and its target reagent concentration or amount delivered (100 μL in the illustrated embodiment). Other information may also be displayed on the screen, as described for screen 64. For example, a user presses a selection button 112, mounted to the housing, for selecting the target volume and concentration, which an internal processor (not shown) in the burette 10 or associated therewith uses to calculate the delivery time. Once the delivery time is over, the tip is automatically retracted into the housing and delivery is halted.

As shown in FIG. 16, a burette of the type shown in FIGS. 8 and 9 can be readily incorporated into a computer controlled system without the need for modifications to the burette 10. Thus a single type of burette can be used in both manual and automated systems. A support, such as a stand 90 is equipped to raise and lower the burette into and from the target liquid 50. The stand is also equipped to rotate the burette about the longitudinal axis through the burette, which results in the tip being rotated in the target liquid. Alternatively, the stand holds the upper part of the burette still, while the lower part or tip is rotated with respect to the upper part with a motor, as described above.

The rotational movement of the burette and the lowering and lifting of the burette by the support 90 is controlled via a computer control system 62, such as a microprocessor with a keyboard 60 and display screen 64. Using the keyboard, the user enters the desired concentration of the reagent in the target solution, the volume of the target liquid 50, and/or other information prompted by the computer screen, such as desired final accuracy and precision. The computer computes the delivery time and controls the delivery process using a clock 44 and by moving the stand 90 between retracted (up) and delivery (down) positions at appropriate times. During delivery, the computer instructs the stand to rotate the burette. As discussed for the embodiment of FIG. 7, the computer control system 62 may also obtain information from the burette via a barcode reader 70, detect the temperature of the target liquid and/or reagent solution, and adjust the delivery time to account for the detected temperature and/or control the temperature of the burette tip and/or target liquid using a heater (not shown) analogous to heater 80.

Figure 17:
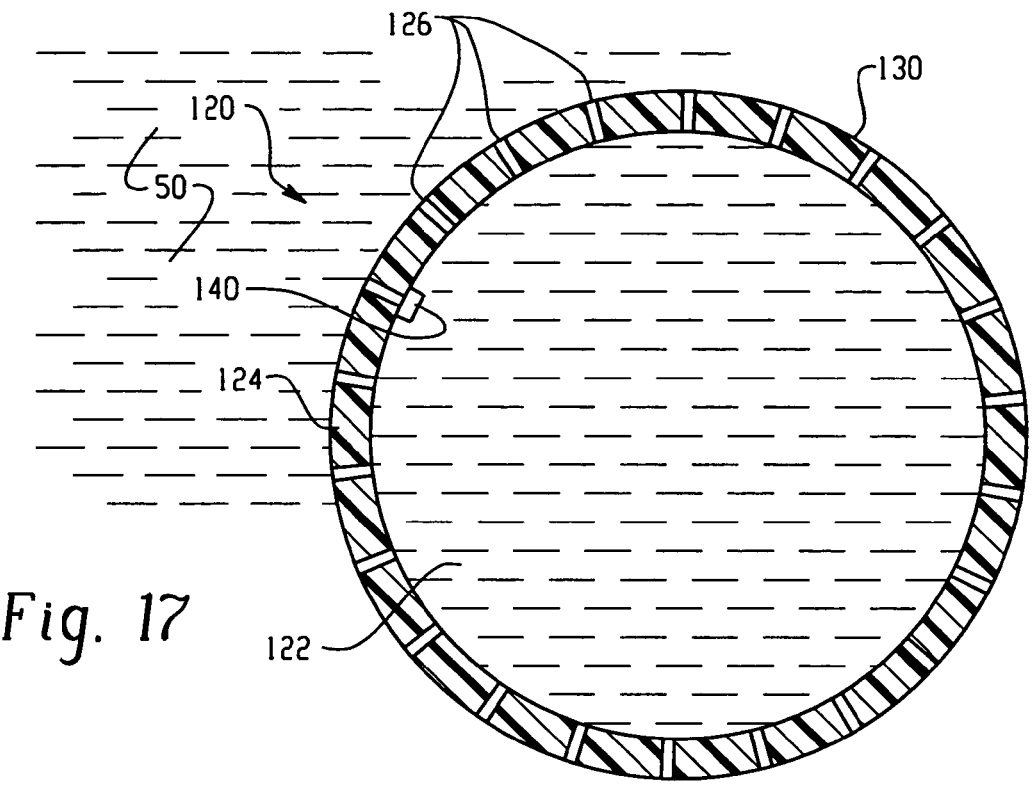
FIG. 17 is a side sectional view of an eighth alternative embodiment of a delivery device according to the present invention.
Figure 18:
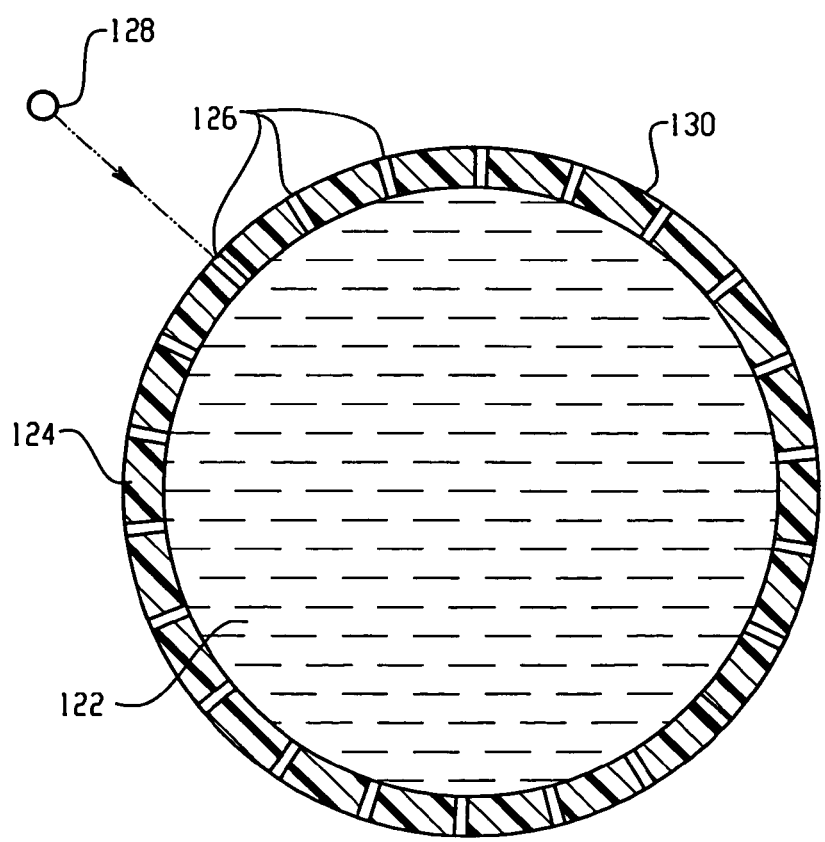
FIG. 18 illustrates one method of preparing the delivery device of FIG. 17.

Another embodiment of a burette 120 shown in FIGS. 17 and 18 is formed by soaking or otherwise infiltrating a porous substrate 122 with the reagent in liquid form e.g., a solution of the reagent in a solvent. The substrate may be, for example, a ceramic substrate or gel, which is preferably chemically inert. Examples of suitable gels include polyacrylamide and agarose. The reagent-soaked substrate is then coated (e.g., by "painting", sputtering, or other means of surface coating or deposition) with a cover layer 124 formed, for example, from a hydrophobic plastic, such as Teflon™, lipophilic PVC, silicone elastomer, or the like, which, after curing, acts as the body of the burette, analogous to body 12 of FIG. 1. One or more regions of the substrate 122 are left free of the cover layer 124 to provide the holes 126 for diffusive delivery. Fabrication of such a burette 120 is relatively easy and generally results in mechanical sturdiness of the resulting burette. It also facilitates the production of extremely small (micron size, e.g., 1-100 micron) delivery ports 126 by removing the coat (or leaving the substrate coat free) at such very small areas only. Microlithography or laser based methods can be used to produce such very small openings in the coating.

In one embodiment, an Excimer laser 128 or other laser is used to form the holes 126 in the cover layer 124 by applying a laser beam which selectively removes tiny areas of the cover layer 124. In another embodiment, a mask is used to define the holes 126. The coating is applied to the mask covered substrate and then the mask is removed.

An alternative fabrication method for the burette 120 employs a device (not shown) having one or more needles of the approximate diameter of the holes. The needle or needles are preferably heated, for example, by resistance heating, or the like, and then used to puncture the cover layer 124.

In one embodiment, the portion of the burette tip 16 that comes into contact with the target solution 50, or optionally the entire burette 10, 120 has a hydrophobic exterior surface 130, provided by the material of the casing 12 or cover layer 124 or by a hydrophobic coating 132 thereon (FIG. 3). This reduces the tendency for the target solution to stick to the burette and minimizes the chance of cross contamination if the burette is used in a subsequent target solution. It will be appreciated that if a hydrophobic target solution is employed, the coating 132/surface 130 is preferably hydrophilic.

The burette 120 of FIG. 17 is also suited for in vivo applications, such as the delivery of a drug or other pharmaceutically active agent into the human or other animal body. The burette 120 may be in the form of a capsule which is ingested, or it may be implanted in the human body. The capsule preferably delivers a drug over an extended period at a slow rate. In one embodiment, the rate is variable. For example, a slow background delivery rate provides a continuous delivery of the drug or other reagent from the capsule (or no delivery, if the background rate is zero). The delivery rate can be changed by including one or more piezoelectric elements 140 which selectively open or close the holes 126. For example, the holes which define the delivery ports are opened by applying an electric voltage or current to the piezoelectric element 140 (or removing an applied electric current).

The burette 10, 120 uses diffusion for reagent delivery. Once convection is blocked (e.g., by suspending the reagent in a gel), and the initial and boundary conditions of diffusion are precisely set, the delivery process occurs in the same way for each burette produced. Thus, reproducibility of such a scheme is virtually unlimited.

The lower limit of the feasible delivery rates is extremely low. For example, values of F of as low as about $10^{-12}$ picoliters per year (equivalent volumetric delivery rate) can be delivered with good reproducibility. For laboratory applications, delivery rates of micromoles to millimoles/hr are readily obtained. It is also contemplated that higher concentrations (in the mM range) into higher target volumes (in the mL range) be delivered by appropriately configured burettes. Practical operational ranges include: reagent or target solution concentrations from the lowest conceivable levels up to 10 mM. Target liquid volumes from femtoliters (fL) up to a few mL, or more are readily accommodated. The lower limits of delivery rates are primarily where the diffusion process occurs on such a small scale as well as rate, that continuum mechanics (thermodynamics) are no longer applicable, and statistical mechanics describe the delivery process. However, this limit is practically unlikely to be reached since delivery is ideal even on the scale of hours, days, or months for delivery and into femtoliter sized target solutions.

Upper limits of delivery rates and larger target volumes can be increased by having a burette with multiple delivery ports 20. Parallel processing in solution preparation (multiple solutions prepared simultaneously) is also feasible with a modified device having multiple, spaced delivery ports 20.

The delivery process is "automatic," or spontaneous in the sense that no mechanical force need be applied to the burette 10, 120. Thermodynamic principles govern delivery. A user of the ready made burette 10, 120 can carry out a solution preparation in a one-step operation, irrespective of how low is the desired solution concentration. For example, by controlling the time of contact between the tip 16 of the burette 10 and the target liquid 50, virtually any quantity can be delivered.

For example, as illustrated in FIGS. 8 and 9, a predetermined amount of a target liquid 50 is delivered to a vessel 100, for example, with a graduated pipette, or other measuring device. The tip 16 of the diffusional burette 10 is inserted into the target liquid. After the predetermined delivery time has elapsed, the burette is removed (FIG. 9).

The delivery rate of the reagent and its dependence on time for the particular burette 10, 120 being used are provided to the user (or are stored in the processor for the delivery device). Solution preparation can thus be achieved with a single control variable: time. Time is a variable whose accurate and precise assessment is much easier than many other variables to control or measure. Timing devices with a high degree of accuracy and precision are available. Preferably, the delivery rate and/or concentration of the reagent are such that the burette 10 delivers quantities of reagent within the user's desired range in a readily measurable and yet convenient time, such as from about 2 seconds to about 5 minutes, more preferably, from about 10 seconds to about 1 minute. Where particularly accurate timing is possible, shorter delivery times are contemplated, such as less than a second. For the burette 120, much longer delivery times may be appropriate, for example several hours, days, or even longer.

The desired accuracy, precision, and preparation speed are generally interrelated: longer delivery times can generally be controlled better.

Since delivery occurs via diffusion, a solution can be formed with substantially no addition of solvent volume to the target liquid 50, i.e., in a preferred embodiment, the reagent diffuses from the burette 10, 120 into the target solution 50, leaving any solvent in which it is mixed behind in the burette. This renders the relevant calculations extremely simple since the volume of the target solution after addition can be assumed to be essentially the same as the volume prior to addition. This is particularly useful in multiple standard addition type analytical schemes. Such schemes are frequently used in measurements involving ion selective electrodes, atomic absorption spectrometry, ICP-MS, and many other analytical techniques, especially when the samples to be analyzed involve complicated matrices (such as serum or blood) that are difficult if not impossible to approximate with any man-made calibration standards. It should be noted that although osmotic pressure differences between the target liquid and the burette reagent solution may cause some solvent movement, this is generally negligible under practical conditions (or is compensated for by an approximately equivalent rate of movement into and out of the burette).

The burette 10, 120 has applications in a variety of fields. It is particularly useful in clinical, environmental, industrial, and research laboratories, in any field that benefits from precise liquid preparations, and especially, in preparation of relatively small volumes. Industrial applications include the chemical and pharmaceutical industries, particularly whenever small batches of reagents are needed, or where the end product, being very expensive, is produced in small batches. Diagnostic applications include clinical, environmental, industrial production and quality control, as well as defense settings. Reactions performed in small scales include research, pharmaceutical, and environmental procedures, as well as where precious materials are processed or produced (such as in the noble metal related industries or in expensive and labor intensive syntheses). The burette can be used to prepare calibration samples for calibrating precise analytical equipment, due to it high accuracy and precision. Moreover, since the burette is amenable to fabrication at relatively low cost and in large numbers, it is suited to use in schools, hospitals, and other settings where large numbers of solutions are to be prepared or where precision measuring equipment or technical expertise is not readily available or is costly to use.

When preparing a solution, considerations generally include: (1) solution volume, (2) desired final concentration, and (3) desired accuracy and precision of the final solution composition. Based on this information, the characteristics of the burette that is best suited for the given task can be derived. These characteristics are used to either design a burette for the given task, or to select one from an assortment of ready-made burettes.

Figure 19:
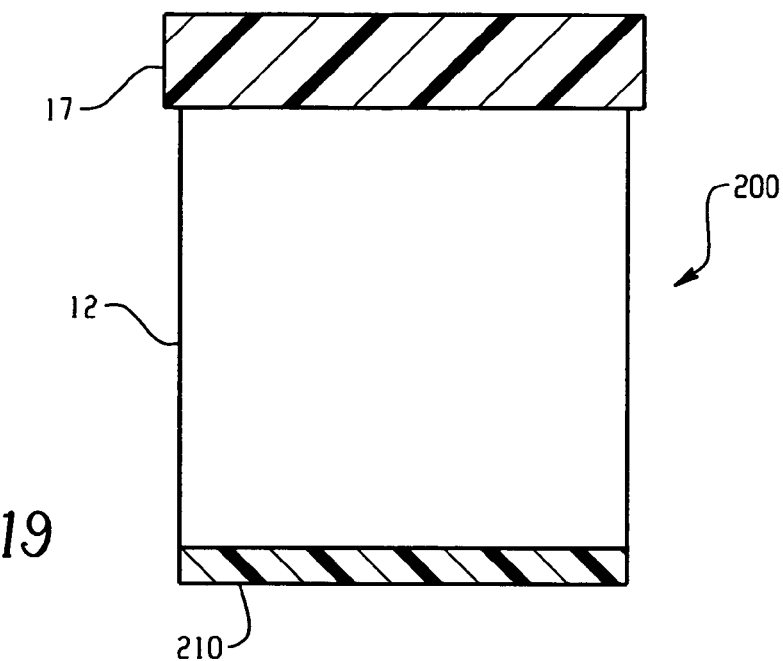
FIG. 19 is a side sectional view of a ninth alternative embodiment of a delivery device.

In one embodiment, a burette 200 is formed with a large, macroscopic, surface area 210 that is active (i.e., delivering the reagent) (FIG. 19). This occurs, for example, with a porous membrane 32 (e.g., a Cyclopore™ membrane) which has a large number of pores, each one delivering reagent, or a where both sides of a macroscopic diffusion membrane, such as cellophane, are effectively stirred. It is also contemplated that a single burette 10, 120 may have two or more interior reagent chambers or barrels 14, each chamber being associated with a separate delivery port 20. Each chamber may hold the same or a different reagent. The ports 20 may be configured to deliver the respective reagent at the same rate or at different rates, for example, by having different sized ports, different membrane materials, and or different size pores.

With reference once more to FIG. 1, the burette 10, 120, 200, 220 may be stored and shipped in a holder 240. The holder provides a closed compartment 242 in which the burette may be placed inside and in which the atmosphere is solvent (e.g., water) saturated. A solvent-saturated environment can be provided by soaking a carrier 244, such as paper tissue, cloth, or the like in a solvent, or by providing a compartment (not shown) that is porous and that contains some solvent. This creates a solvent vapor rich gaseous environment without allowing the solvent to come into contact with the burette tip 16. The atmosphere itself can be air. If the reagent is one which is deteriorated by oxygen, an inert gas, such as nitrogen or noble gas may be used. In some circumstances, damage to the burette may result from use of water or other pure solvent because a high concentration salt, or acid, alkali, or the like is stored inside the burette, which may slowly absorb water or other solvent inside from the water saturated atmosphere in the burette holder. In such circumstances, it is preferable for the carrier 244 or porous compartment to contain the same solution as is inside the burette to saturate the air around the burette. This also reduces the risk of contaminating the burette if, for example, physical contact during storage and shipping occurs between the burette tip and the carrier solvent or solution. By using the same solution for the carrier and burette, such risks are minimized.

To ensure that the contents of the burette remain sterile, particularly when the burette is to be stored for some time prior to use, or contains a salt solution prone to microbial growth, the solution providing the atmosphere in the holder 240 may include an antimicrobial agent.

The construction of the burette tip may vary according to the chemical to be diffused. The burette material should be compatible with the reagent which is to be diffused, e.g., acids and oxidizing reagents may use different materials. For light sensitive chemicals, an opaque casing 12 or a housing 107 may be used.

While the invention has been described with particular reference to small membranes 32 covering a conical tip 16 of a burette, it is also contemplated that large, flat membranes may be used, although as discussed below, ensuring a Nernstian concentration profile within the membrane and on both sides (e.g., by stirring the liquid on both sides of the membrane) may make the design internally and externally more complicated. By "Nernstian," it is meant that the profiles do not change appreciably in time, allowing for a constant delivery rate.

It will be appreciated that although the system has been described generally in terms of delivering a single reagent, multiple reagents can readily be delivered, either from a single burette (e.g., by combining both reagents in a single solution), or by using multiple chambers, each one attached to the same delivery port or to a separate delivery port, such that the reagents are simultaneously delivered when the delivery port or ports are placed in contact with the target liquid.

In another application, one of the burettes described herein is used in combination with a feedback system which monitors a change in a property of a target solution (e.g., ISE spectrophotometry, fluorescence, visible property, such as color change, pH electrochemical measurement, or the like). The feedback system determines the concentration of the reagent in the target solution from the detected change and provides feedback in the form of a signal to the burette to stop delivery when a desired concentration is reached. With such a system, calibration of the burette can be eliminated.

In another application, a multicomponent solution is prepared by having separate different delivery ports which are started and stopped at appropriate times to prepare a predetermined multicomponent target solution.

Theoretical Considerations

In designing a burette the following considerations are made: (1) the initial and boundary conditions that use of the burette entails; (2) the delivery rate and its dependence on (contact) time as applicable for the specified initial and boundary conditions; and (3) the total amount of deliverable species (reagent) in the burette body 12.

Where the shoulder region 18 is wider than the tip 16, this "limits" the rate limiting step into the tip region. For conventional pipette tips, such as an Eppendorf type of plastic pipette tip there is no widened shoulder, only a conical tip which extends from a body. For conventional pipettes, the Cottrellian analysis of the pipette is the same as that of a microdisk electrode, except that the solid angle of the space considered is much smaller than the full sphere of a microspherical electrode or semisphere of a microdisk electrode. A steady state solution to this (spherical, semispherical, or conical) mathematical diffusion problem is possible, but it takes time to reach it. The steady state solution can be computed based on the steady state term of the microelectrode equation, as described in greater detail below.

In the present case, it is desirable to reach steady state conditions as quickly as possible, thus ensuring a constant delivery rate.

First the case is considered in which it is assumed that the inside of the burette is "semi-solid", meaning a gel 22 or a porous substance (like ceramic) is present that contains the reagent solution, so that there is no considerable convection inside the burette.

For such burettes one possible realization is very similar to a cylindrical tip, which has a very small hole at the end, or near the tip end (FIG. 12A).

Therefore, a Cottrell type equation (Equation 1) describes reagent delivery where it is assumed the reagent concentration outside the burette to be negligible:

$$F(t) = \text{Cottrell transient} + \text{steady state microelectrode term} \quad (1)$$

where F(t) is reagent flux or delivery rate into the target solution, t is time with t=0 at the moment when the delivery port 20 touches the target solution. More accurately, for Equation 1 to be valid, reagent concentration inside the target solution should be always negligibly small (during the entire operation) compared to the burette bulk reagent concentration. This assumption is valid, however, for almost any type of practical application.

The delivery at time zero, t=0, will have a very high rate but only for an infinitesimally short time period. In practice, this means a very short time, negligible compared to the duration of the entire delivery operation. After the initial burst, the delivery rate decays rapidly to reach a steady state at a rate that corresponds to the stationary term of the Cottrell type "microelectrode" equation (steady state, second term microelectrode term in Equation 1).

The transient which occurs before stationary operation is reached has a duration which is roughly proportional to the diameter d of the delivery port opening. If the diameter d is in the order of 10-30 microns then we can assume that the depleted region inside the burette at steady state will be about 100 microns thick. This, for usual diffusion coefficients, means that the transient term (Cottrell transient in Equation 1) decays within about 100-200 milliseconds, which is a very short time, and is therefore negligible for most practical designs and operation. However, for larger openings (e.g., about 100 microns to 1 mm), this transient time is larger, and may be on the order of several minutes. For such cases, calibration of the burette preferably includes an assessment of the transient. Between each delivery time period, a time period sufficient to reestablish uniform concentration in the burette is allowed to pass. Alternatively, a second or subsequent delivery is commenced immediately after the previous delivery is completed so that the steady state conditions which have been achieved in the first delivery are maintained. Alternatively, the burette tip is stored in contact with a large reservoir of buffer to allow continued delivery between two actual reagent making operations. In all these cases, identical or substantially identical initial conditions can be achieved for each delivery. This ensures reproducibility of the delivery process which is important for achieving accuracy. This makes burette calibration valid for each subsequent delivery process.

While any reproducible delivery curve can be used as long as the desired reproducibility is provided, in practice, best results are obtained when the transient at the beginning of each delivery is negligible with respect to the entire duration of the process. It is possible to design a burette for a given reagent such that term 1 (Cottrell transient) in Equation 1 is negligible with respect to term 2 (steady state term). Thus, in practice, linear (constant rate) delivery is possible within a reasonable tolerance.

Where the transient term is not negligible, there may be a short waiting period before a burette can be reused again after a delivery operation. The initial conditions to satisfy the above equations should be valid at the beginning of the next operation for reproducible deliveries. The waiting period allows reagent concentration to become homogeneous again inside the burette. For most accurate results, homogeneous conditions should be established as perfectly as possible. Therefore, this waiting period is preferably twice as long, and, more preferably, at least three times longer than the duration of the initial transient in the equations. For example, if the transient is about 50 milliseconds long then this requirement is easy to fulfill and does not make any practical difference. If it is several minutes, however, then a waiting period in the order of 10 minutes between two subsequent uses of the same burette may be appropriate. Preferably, the tip is constructed such that the waiting time is less than one minute, more preferably, less than ten seconds, most preferably, about one second or less, such that an operator is not likely to cause an error in delivery by inadvertently using the burette before the waiting time has elapsed. Alternatively, the delivery device may be programmed to provide an alarm or an ALL CLEAR signal when the waiting time is over.

Preferably, the membrane and gel (where present) are selected such that the transient term is 1 second or less, such that, after a period of contact of less than 1 second, the reagent diffuses into the target liquid at a substantially constant rate (i.e., the reagent delivery rate does not vary by more than 10%, preferably, no more than 5%) throughout the delivery period).

The above considerations apply to relatively small molecules (i.e., those having a molecular weight of about 5000, or less). For larger molecules, the diffusion coefficient may decrease such that the molecule may take several minutes to travel a distance of a few tens of microns. In such cases, the transient time may still be significant and should be taken into consideration, particularly where a high degree of accuracy is desired. This means that a simple linear R(t) calibration may not suffice. However, a nonlinear one can be generated which achieves very good accuracy. It has been found that decreasing the diameter d of the tip and tube 18, allows larger molecules to be used with greater accuracy.

Using the diffusional burette instead of a conventional method for making a solution is useful for cases when the target solution cannot be made without more than one dilution. If the target solution can be made by weighing materials on a balance, these can be dissolved in a flask, and diluted perhaps once more, then a conventional method can readily be used for its preparation. Once two or more consecutive dilutions are needed, i.e., when the target concentration is low, then the burette 10 becomes a useful tool to produce the desired (low) concentration in the target solution in a single step, precisely and accurately. This step consists of immersing the tip of the burette in the target solution for a predetermined period and then withdrawing it. In this case, i.e., when this same solution would have required two or more dilutions to make, it is unlikely that the burette itself will get depleted of the delivered substance to an extent larger than negligible.

Figure 26:
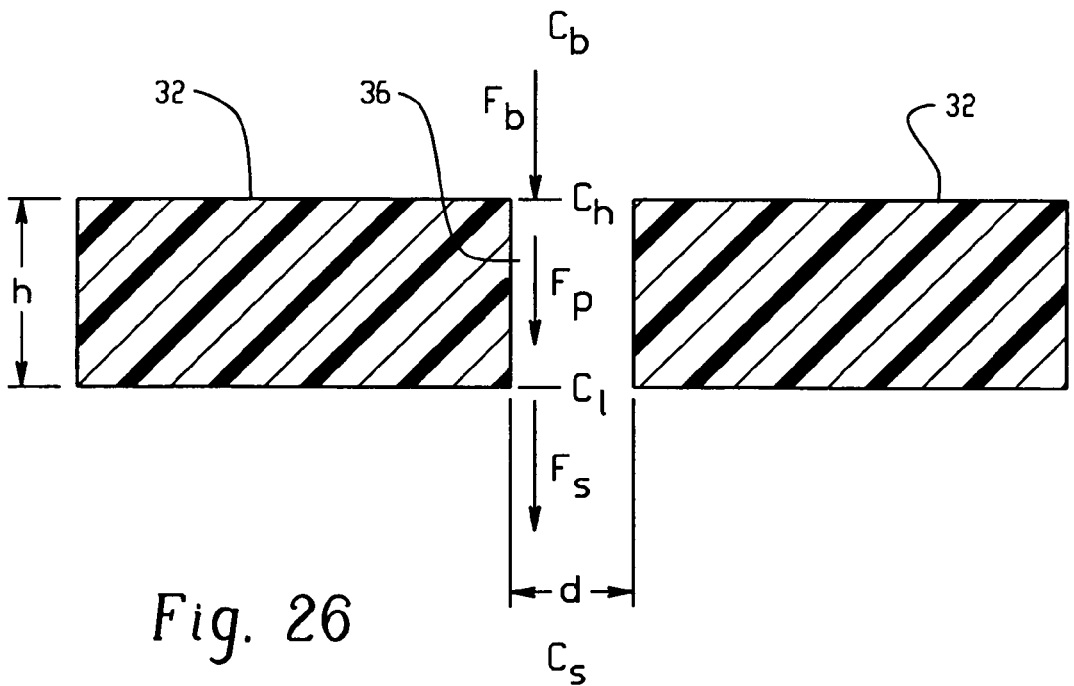
FIG. 26 is a schematic view of a delivery port of a diffusional burette according to the present invention.

For such applications, the equations that describe the diffusional burette operation and help designing actual burettes are as follow and are illustrated schematically in FIG. 26, where: F is flux, c is concentration, subscripts b, h, l, s are as follows: b stands for burette bulk, h stands for inner or burette end of a pore 36 in the delivery membrane, l is lower or outer end of the pore, and s is in the bulk of the target solution. D is diffusion coefficient (considered here the same for burette, pore 36, and solution, for the same chemical), r is pore radius, d: pore diameter, A: cross sectional area of pore, and z is membrane thickness=pore length. Concentration in solution bulk, $c_s$, is virtually zero. With these conventions:

1. Steady State Operation of One Pore within the Burette Delivery Membrane is Described as

| | |
|---|---|
| $F_b = 4Dr(c_b - c_h)$ | flux from burette body into pore |
| $F_p = (AD/z)(c_h - c_l)$ | flux across pore |
| $F_s = 4Drc_l$ | flux from pore into target solution |

In steady state, all these fluxes are equal and the same. This defines two equations with two unknown variables ($C_h$ and $c_l$) which can be solved:

$$c_h = [(4 + \pi d/2z)/(4 + \pi d/z)]c_b$$

$$c_l = [(\pi d/2z)/(4 + \pi d/z)]c_b$$

From these, delivery flux by one pore is:

$$F = D[(\pi d^2/z)/(4 + \pi d/z)]c_b$$

This gives, for a very wide pore ($d/z \to \infty$): $F = D d c_b = 2 D r c_b$ and for a very narrow pore ($d/z \to 0$): $F = 0$ Burette delivery rate is then F times the number of pores.

2. Effect of Flow in the Solution on Delivery Rate:

Calculating the relative concentration drop within the pore compared to the entire concentration drop from burette bulk to solution bulk, i.e., $R = (c_h - c_l)/c_b$, estimates the extent to which transport within the pore is rate limiting. For example, if R=78% then 11% of total concentration drop from burette bulk to solution bulk drops within the burette approaching the pore, 78% drops within the pore, and 11% drops within the solution adjacent to the pore. The more of the entire concentration drop is confined to within the pore the less sensitive delivery rate will be on eventual flow in the target solution. As an example, for a 10 micron thick membrane (z=10 microns) the following can be calculated, as shown in TABLE 1:

TABLE 1

| d (microns) | R (%) |
|---|---|
| 100 | 11 |
| 10 | 56 |
| 1 | 92 |
| 0.1 | 99 |

This means that a pore 36 which is 10 microns long and 0.1 microns (=100 nm) wide will confine 99% of the entire concentration drop to within itself. This is excellent because flow dependency is then practically eliminated.

3. Transient Duration

Another characteristic to be considered is how fast the initial transients die out after immersing the burette tip into the target solution. The faster this happens, the quicker steady state delivery develops. This is characterized by the above equations and estimated flux. This flux is a constant, meaning a constant, predictable, and known delivery rate and a linear calibration. The longer the transients are, the more effect they will generally have on the ultimate amount delivered, and the less predictable the amount delivered tends to be.

From Table 1, it is clear that narrow and long pores are preferred (e.g., d/h=0.1 or less) for avoiding flow dependency. In this case almost the entire transient will consist just of the transient within the pore and the transients in the two adjacent areas (burette and solution) will die out much faster. Therefore it is sufficient to consider transient duration within the pore. This is approximated by:

$$t_{transient}=z^2/D$$

If this value is much smaller than the total duration of reagent delivery then transient effects are negligible. For example, for a 10 microns thick membrane (10 microns long pores, or z=10 microns) and for a small ion ($D=10^{-5}$ $cm^2/s$):

$$t_{transient}=10^{-6}\ cm^2/10^{-5}\ cm^2/s=100\ ms=0.1\ s$$

Thus, a delivery time of as short as 10 seconds is long enough to make transients negligible (100 ms is 1 % of total delivery time).

Some bias due to excess delivery during the transient may also be incorporated in the calibration. This excess is known and can be added to an otherwise linear calibration. For example, for a 100 second delivery in the above example, the transient will only be 0.1% of total delivery and therefore any bias is negligible. For a 10 second delivery, however, it may be desirable to account for the 1% of delivery time, which is spent in the transient, in the calibration. For the example above and using a 1 μm diameter pore, the excess amount can be calculated as:

$$\text{Bias}=c_b\,z\,\pi d^2/3=10\ \mu m\ \pi 1\ \mu m^2\ c_b=10\times 10^{-12}\ cm^{3\ i}\ {}^{c}{}_{b}=(10^{-11}\ mL)c_b$$

Using a burette filled with a 1 M=1 mmol/$cm^3$=1 mmol/mL reagent, this yields:

$$\text{Bias}=10\ \text{picomol}$$

As long as the pore is used to deliver many times more than this amount, the bias can thus be neglected. If it needs to be taken into account, however, then the following calibration can be used:

$$N(t)=(3\ \text{Bias}/t_{transient})t+\text{Bias}$$

where N(t) is the delivered amount during time period, t; t=0 at the instant of immersing the burette into the solution. For the given example, this translates to $$N(t)=(3\times 10^{-11}/0.1\ s^{-1})t+10^{-11}\ \text{moles}=3\times 10^{-10}t+10^{-11}\ \text{moles}=300t+1\ \text{picomoles}$$

where t is the time in seconds. Thus the excess amount delivered during the initial transient is only 0.33% of the total amount when a 10 second delivery is considered and only 0.03% for a 100 second delivery. In most cases, the bias can thus be neglected.

To determine the delivery time for achieving a selected target solution concentration from a conical tip, as shown in FIG. 1, the following equation can be used, $$C(t)=Cr(1-\exp[-B \cdot t/V]) \text{ where } B \approx D \, r \, \Pi \tan \theta \quad (5)$$

and where C(t)=the concentration of the reagent in the target solution at delivery time t
Cr=concentration of the reagent within the burette
V=volume of the target solution
B=a geometric factor (dependent on the shape of the burette tip)
D=diffusion coefficient of the reagent molecules being delivered
r=radius of hole in burette tip
θ=cone angle (see FIG. 2)
t=time, being zero at beginning of delivery
For example, for ferriyanide, if
$D=7.3 \times 10^{-6}$ cm$^2$/s
r=0.04 cm
θ=12.5°
then, $B=2.03 \times 10^{-7}$ cm$^3$/s
Since c(t)=R(t)/V
then the actually valid expression can be substituted into R(t); this for the above conical tip would make $$B = D \, r \, \Pi \tan \theta$$

which is steady state flux in this case, so it would make:

$$c(t)=\text{const flux times } t/V$$

Since the diffusion coefficient D is dependent on temperature, the value of D for the actual delivery temperature should be used in the equation (or a correction factor for the temperature). Preferably, the burette is operated at a constant temperature such that D remains a constant. The diffusion limiting membrane is applicable to a conical design of tip and also to other embodiments.

In one embodiment, a burette 200 is formed with a large, macroscopic, surface area 210 that is active (i.e., delivering the reagent) (FIG. 19). With such a delivery system, larger volumes can be achieved. For example, when delivering the reagent from a larger area of which the surface is coated with a planar diffusion limiting coat (e.g., "painted" on a semi-solid burette interior—see FIG. 17) or any other layer similar to a limiting membrane, then macroscopic delivery rates can be achieved. To avoid the effect of a transient, depletion should not propagate far outside of this membrane 210 in either direction. Therefore, we still have the same condition fulfilled, i.e., that almost all gradient will drop within a very thin layer. In this case, reproducibility as well as negligible waiting (transient) times are feasible with rates similar to mechanical delivery tools.

The transient time can be eliminated, for all practical purposes, by providing a flat section of the burette tip in which there is one, or a number of, very small hole(s) and the holes are filled with a diffusion limiting membrane (FIGS. 4, 12). This provides a flexible design, the number of holes being selected according to the desired delivery rate range, with exactly the same dynamic characteristics. A number of similar small holes provides an array of very small sources. The number of holes is generally proportional to the delivery rate as long as the distance between the holes is larger than the extension of the depletion (same as the semispherical region of non-uniformity, see above) around such a hole. Thus:

$$C(t)=n \, Cr(1-\exp[-B \cdot t/V]) \text{ where } B \approx n \, D \, r \, \Pi \tan \theta \quad (6)$$

where n is the number of holes

Depletion refers to that both inside the burette and in the target solution. The array of holes 36 can be seen as analogous to a microelectrode array that has its own particular mechanism of mass transport. Another advantage of this approach is that steady state operation is generally reached within milliseconds when the holes are very small (in the few microns range). This means a very negligible initial burst at the beginning, yet enabling high macro flux analogous to the macro current for a microelectrode array. It has been found that equations valid for such microelectrode arrays can be applied to delivery from a burette by replacing electrical current with molar flux.

In each of these design approaches, the homogeneity of the target solution 50 may be a factor, and thus for high accuracy and precision, stirring or otherwise homogenizing the target solution is optionally provided by a stirring means. Homogenizing helps to ensure that the burette is function ideally during the entire duration operation (i.e., delivery is closely approximating that predicted from theory). Validity of the ideal equations (see above) is based on the assumption that the concentration in the target solution locally, adjacent to the hole or membrane of the burette, is zero (or negligible), as compared to the concentration in the body of the burette. This assumption is satisfied in many situations. For example, in the case of a conical burette tip, there is a huge solid angle of water or target solution outside the tip into which the delivered molecules rapidly diffuse away from the burette. In such cases, stirring is not generally necessary to achieve this condition. However, in the case of a large flat membrane with diffusion coefficients not much lower than in water, then stirring ensures that the reagent is dispersed at a sufficient rate to ensure the validity of the equations. Inside the bulk of the burette there may also be a need for stirring to achieve the former mentioned condition.

Stirring also has an advantage in that it is generally desirable for the target solution to be homogenous at the end of delivery. Stirring can be obtained in a variety of ways, such as with a magnetic stirring bar inside the target solution. However, when it is desired to produce very precise solutions of very small volumes and sometimes very low concentrations, other stirring methods may be appropriate as in some circumstances, as a stirring bar can cause cross contamination between different solutions, for example, the solution is in a container 100 which is stirred by an external vibrating mechanism 104 (FIG. 5). Another alternative method of producing stirring in the solution is to move the burette, e.g., by rotating or vibrating the burette. As shown in FIG. 7 a vibrating mechanism 106 causes a small vibration or rotation of the tip 16. FIG. 12 shows a rotation of the tip itself.

Movement of the burette tip 16 can be in a horizontal or vertical direction. Or, the burette 10, 110 may be moved in a circular motion, or in other directions. Preferably, the direction of the vibration is not perpendicular to the plane of the membrane 30 or delivery hole or surface, as in some cases, this may induce some (variable) pressure on the membrane leading to damage of delivery area and thus delivery is less accurate. Preferably, there is at least about 20°, more preferably, at about a 45° angle between the plane of the hole and the direction of the vibration. For example, vertical or horizontal vibration or movement is preferred if the delivery holes are in a tilted side of the burette tip (like tilted by 45° at the tip). To avoid mechanical wave resonance in the target solution resulting in amplification of the vibration, a vibration source 104, 106 which provides vibration which is generally random in nature, i.e., in amplitude, frequency, and direction may be employed. Such "random" vibrations, may be produced, for example, by employing a random generator in a microprocessor 62, 62' controlling the vibration mechanism 104, 106.

Another option is to provide stirring of the reagent inside the burette. While this is generally not possible when the reagent is soaked and stored in a porous or gel-like substrate, where the reagent is in a liquid form, stirring may be employed. Stirring inside the burette is particularly effective where a planar diffusion membrane is used as the active surface of the burette. In this case, vibration of the burette 10, 110, 200 both stirs the interior reagent and also stirs of the surrounding target. Where stirring is used, the membrane need not be diffusion limiting to provide a high degree of accuracy and precision. The membrane may thus have a high diffusion coefficient yet function efficiently. This is because the diffusion is confined to the membrane, in this case, not by a low diffusion coefficient, but by both solutions (reagent in burette, and target solution) having agitated convection on both sides of the membrane. This may be advantageous when a high delivery rate is desired.

As discussed above, for an arrangement in which the burette tip has multiple holes 36, it is preferable that there be little overlap, more preferably, no overlap between the depleted domains of adjacent holes inside and outside the burette. This is readily achieved for a short time with even relatively large openings or delivery ports such as, e.g., 200 microns. For example, the holes may be about 0.1 to 2 mm apart.

Without intending to limit the scope of the invention, the following Examples demonstrate preparation of a diffusional burette

EXAMPLES

Example 1

Preparation of a Ferricyanide Delivery Burette

Figure 24:
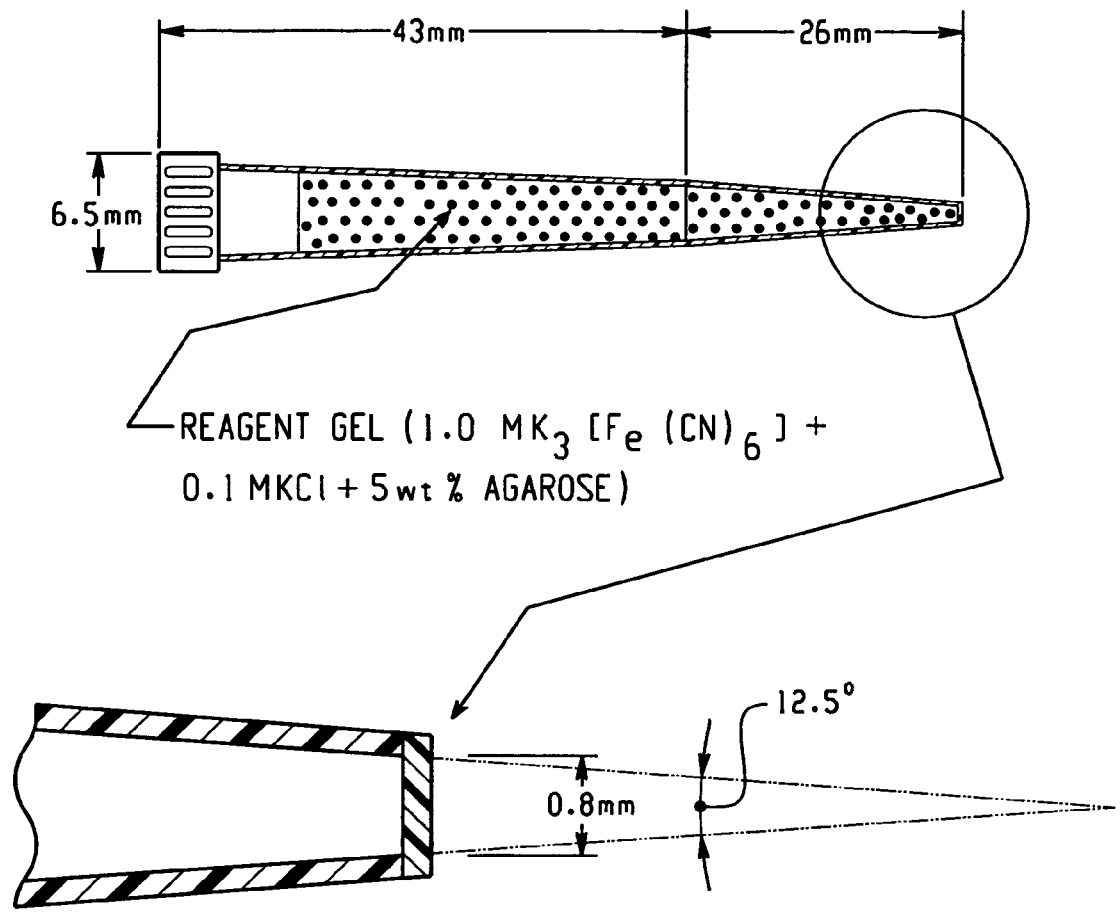
FIG. 24 shows the dimensions of an exemplary burette.

Ten mL of an aqueous solution containing 3.29 g of $K_3$[Fe(CN)$_6$](P-3667 Sigma) and 74.6 mg of KCl (P217-500, Fisher Scientific) was prepared. To this solution, 0.5 g of a gelling agent, agarose (A-6013, Type 1: Low EEO [9012-36-6], Sigma) was added. This mixture was heated up to 80° C. until the solution becomes clear. One mL of this solution was filled into a micropipette tip (101-1000 μL, 2 13/16 inches, Eppendorf style, 21-375E, Fisher Scientific) and allowed to stand at room temperature until the filling solution became gel. The detailed dimensions of the thus prepared ferricyanide delivery burette are shown in FIG. 24.

Example 2

Preparation of a Potassium Delivery Burette

Ten mL of an aqueous solution containing 74.6 mg of KCl (P217-500, Fisher Scientific) 5.84 mg of NaCl (S-9625, Sigma) and was prepared. To this solution, 0.5 g of agarose (A-6013, Type 1: Low EEO [9012-36-6], Sigma) was added. This mixture was heated up to 80° C. until the solution becomes clear. 200 μl of this solution was filled into a micropipette tip (1-200 μL, 1 7/8 inches, Eppendorf style, 21-375D, Fisher Scientific) and allowed to stand at room temperature until the filling solution became gel.

Example 3

Ferricyanide Delivery

Figure 20:
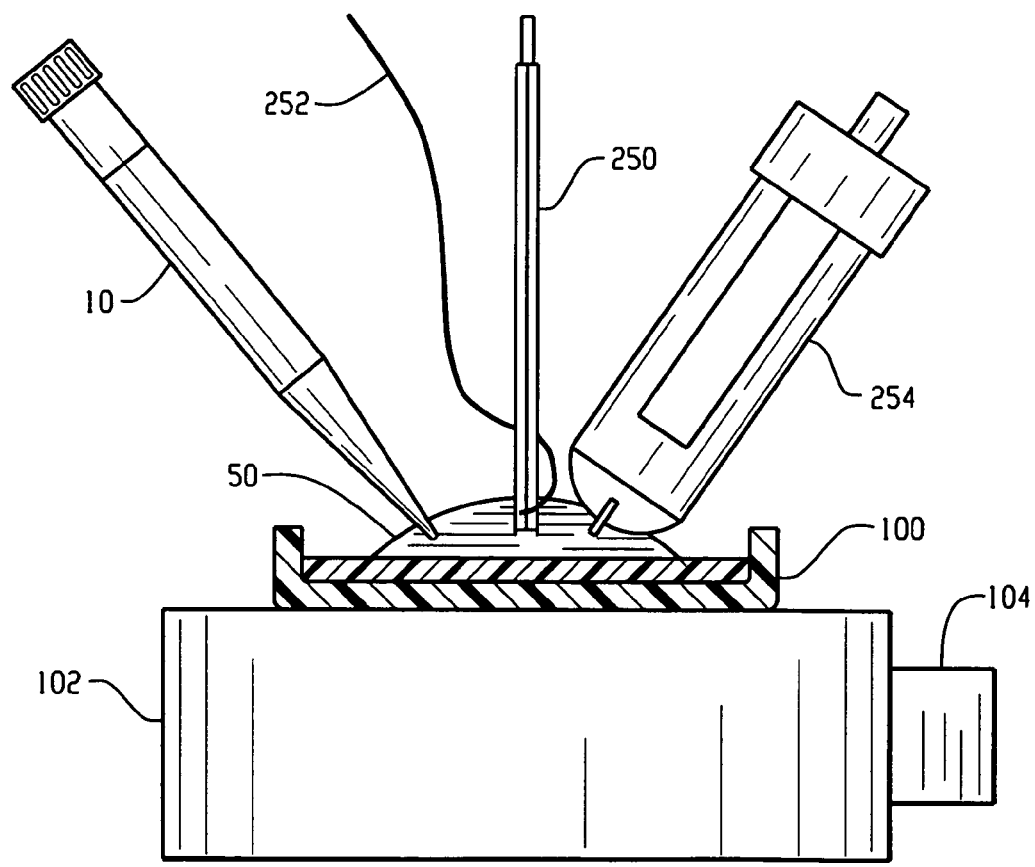
FIG. 20 is a side view of a delivery and monitoring system for evaluating the delivery devices according to the present invention.
Figure 21:
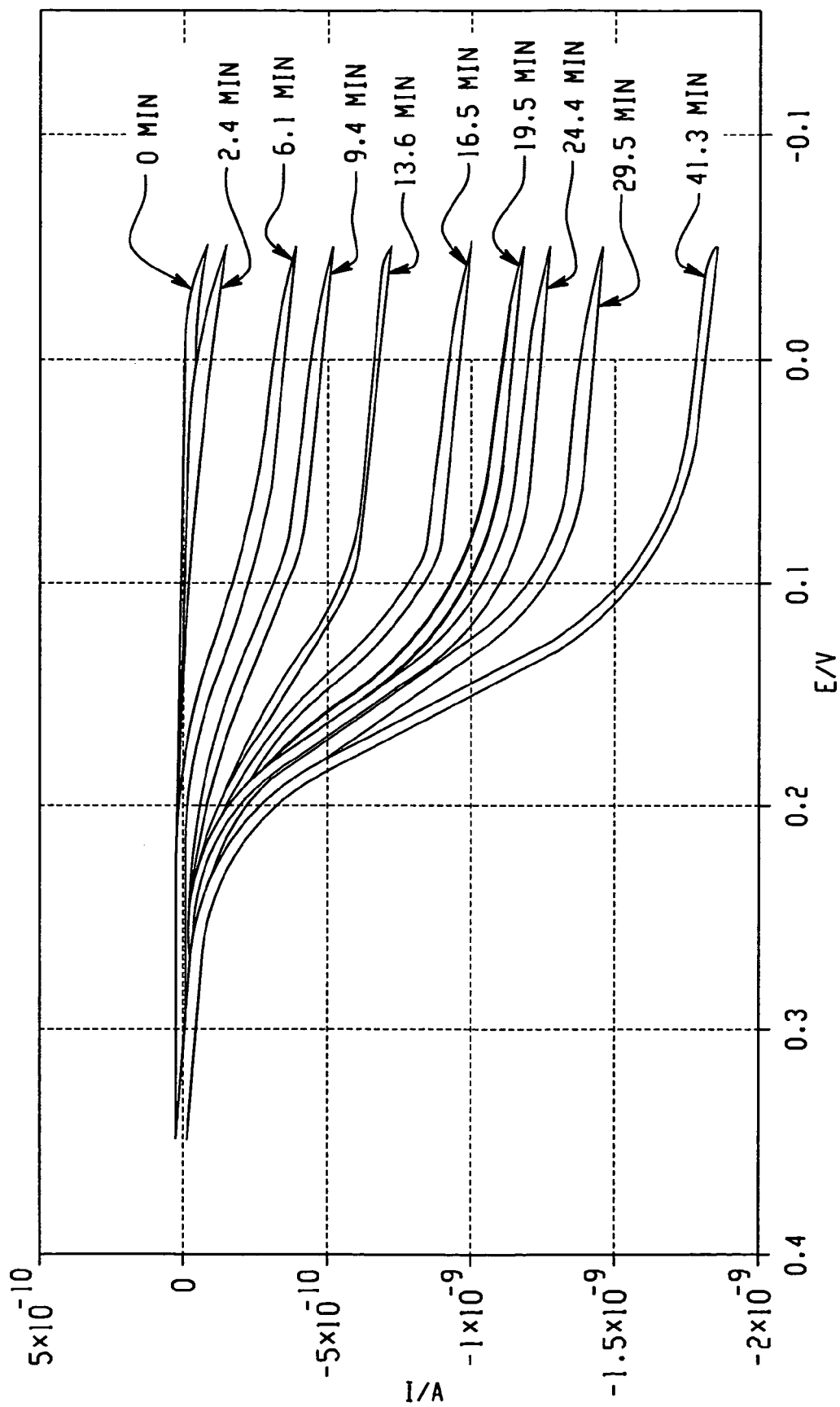
FIG. 21 is a plot of cyclic voltammograms showing current in amps vs. electrode potential in volts for ferricyanide delivery times between 0 and 41.3 minutes.
Figure 22A:
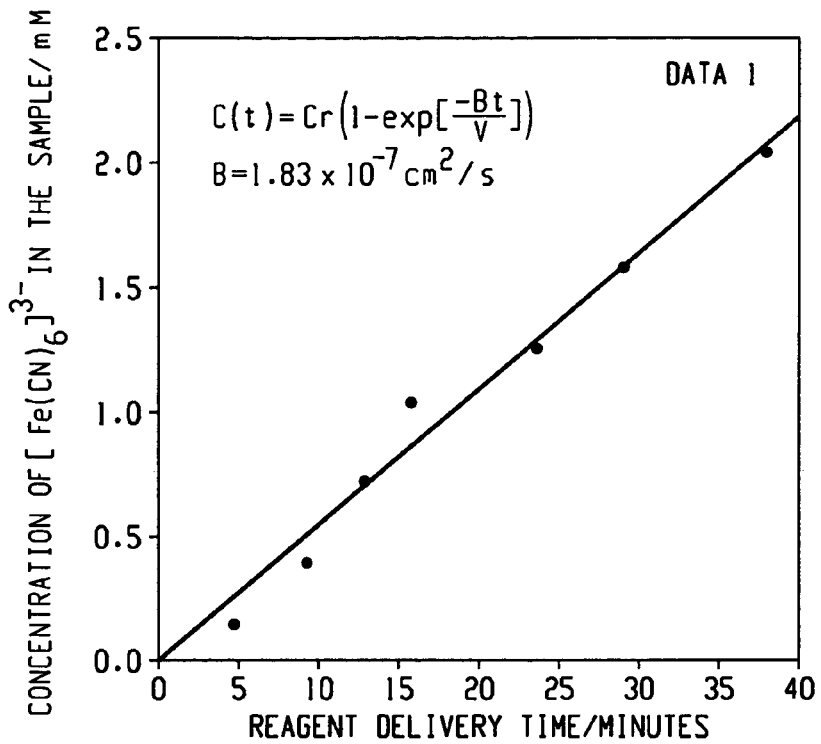
FIGS. 22a, 22b, and 22c show plots of concentration of ferricyanide in a fresh target solution in mM vs. reagent delivery time in minutes for three sequential delivery procedures from the same burette.
Figure 22B:
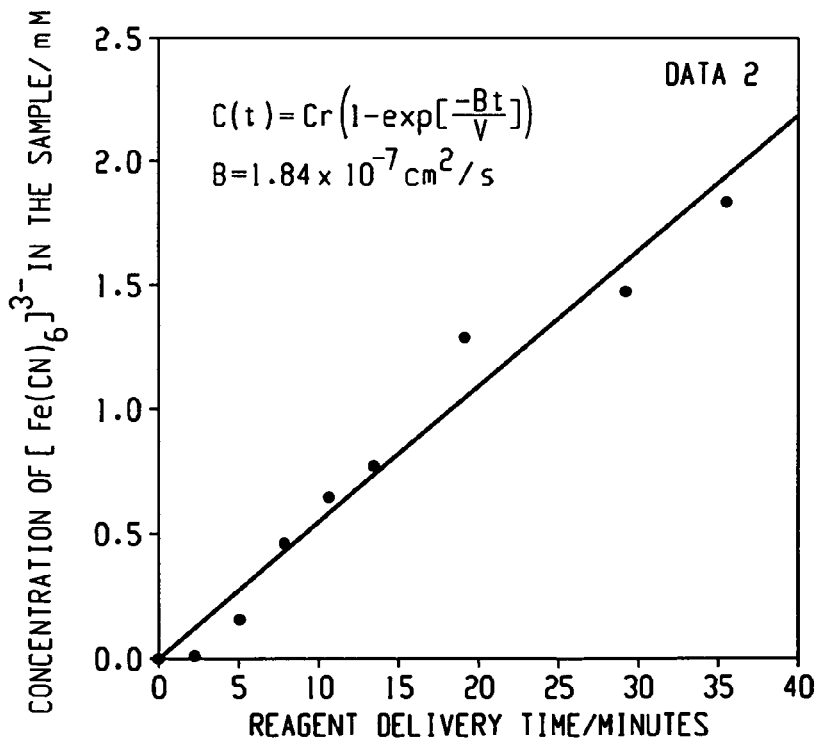
Figure 22C:
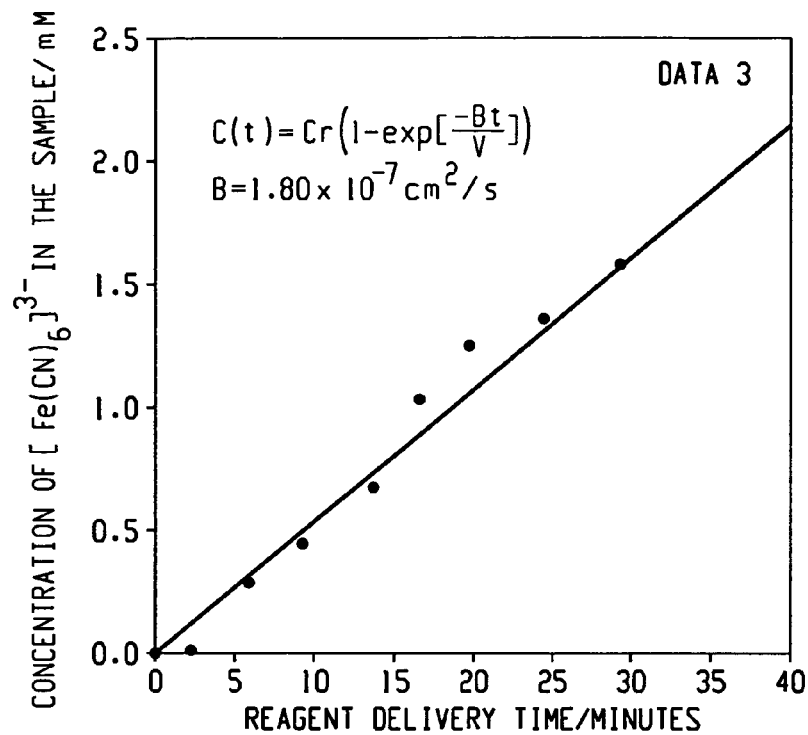

A ferricyanide burette was prepared as for Example 1. FIG. 20 shows the experimental setup for ferricyanide (and potassium) ion delivery. 200 μL of 0.1M KCl aqueous solution was used as a sample (target) solution 50. The solution 50 was placed in a container having a silicone elastomer liquid support surface. To monitor the delivered ferricyanide concentration into this sample solution, a micro Pt electrode 250 8 μm in diameter was used in combination with a counter electrode 252 formed from stainless steel wire and a reference electrode 254 (BAS Ag/AgCl microreference electrode). The cyclic voltammograms for various delivery times from 0 to 41.3 minutes are shown in FIG. 21. The current due to reduction or rather, electro-reduction of ferricyanide increases with increasing delivery time, indicating successful reagent delivery with the prepared diffusional burette 10. FIG. 22 shows three sets of the ferricyanide delivery results obtained by using the same burette (labeled data 1, data 2, and data 3, respectively). Linear relationship between the delivered ferricyanide concentration in the sample solution and the delivery time was found in each set of data, as shown in plots 13a, 13b, and 13c. Table 1 lists five sets of data for the delivered ferricyanide concentrations after 15 minutes reagent delivery by using the same burette. Very good reproducibility of the reagent delivery was obtained with 0.020 mM as the standard deviation. This result demonstrates the potential of this diffusional burette for the quick and accurate preparation of standard sample solutions.

TABLE 1

| Run | Conc. Of [Fe(CN)$_6$]$^{3-}$ in the Target Solution |
|---|---|
| 1 | 0.778 mM |
| 2 | 0.821 mM |
| 3 | 0.793 mM |
| 4 | 0.817 mM |
| 5 | 0.825 mM |
| Average | 0.807 mM |
| Standard deviation | 0.020 mM |

Example 4

Potassium Delivery

Figure 23:
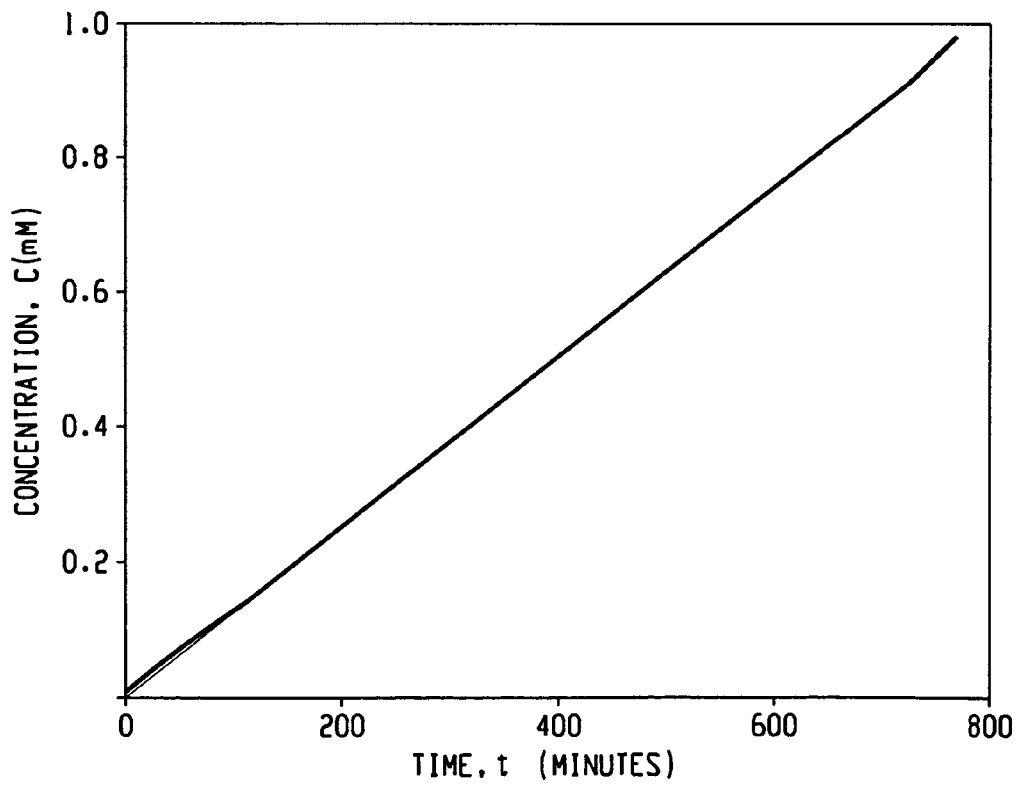
FIG. 23 is a plot of potassium ion concentration in mM in a target solution measured by a $K^+$ ion selective sensor delivered by a burette during continuous delivery.

A diffusional burette for delivery of potassium (and chloride) ions was prepared for Example 2. Ten mL of 0.01M NaCl aqueous solution was used as a target solution. To monitor the delivered concentration of potassium in the sample solution, a liquid membrane-type ion-selective electrode based on valinomycin was used in pace of the platinum electrode system of FIG. 20. FIG. 23 shows the relationship between the delivered potassium concentration in the sample solution and the delivery time. The plot does not show actual data points but is derived from data obtained every one to two minutes and fitted to the curve shown by the least squares method ($C=12\times10^{-4}$ t+$8.0\times10^{-4}$t$^{0.5}$). Almost perfect linear relationship was observed.

Example 5

Potassium Delivery

Figure 25:
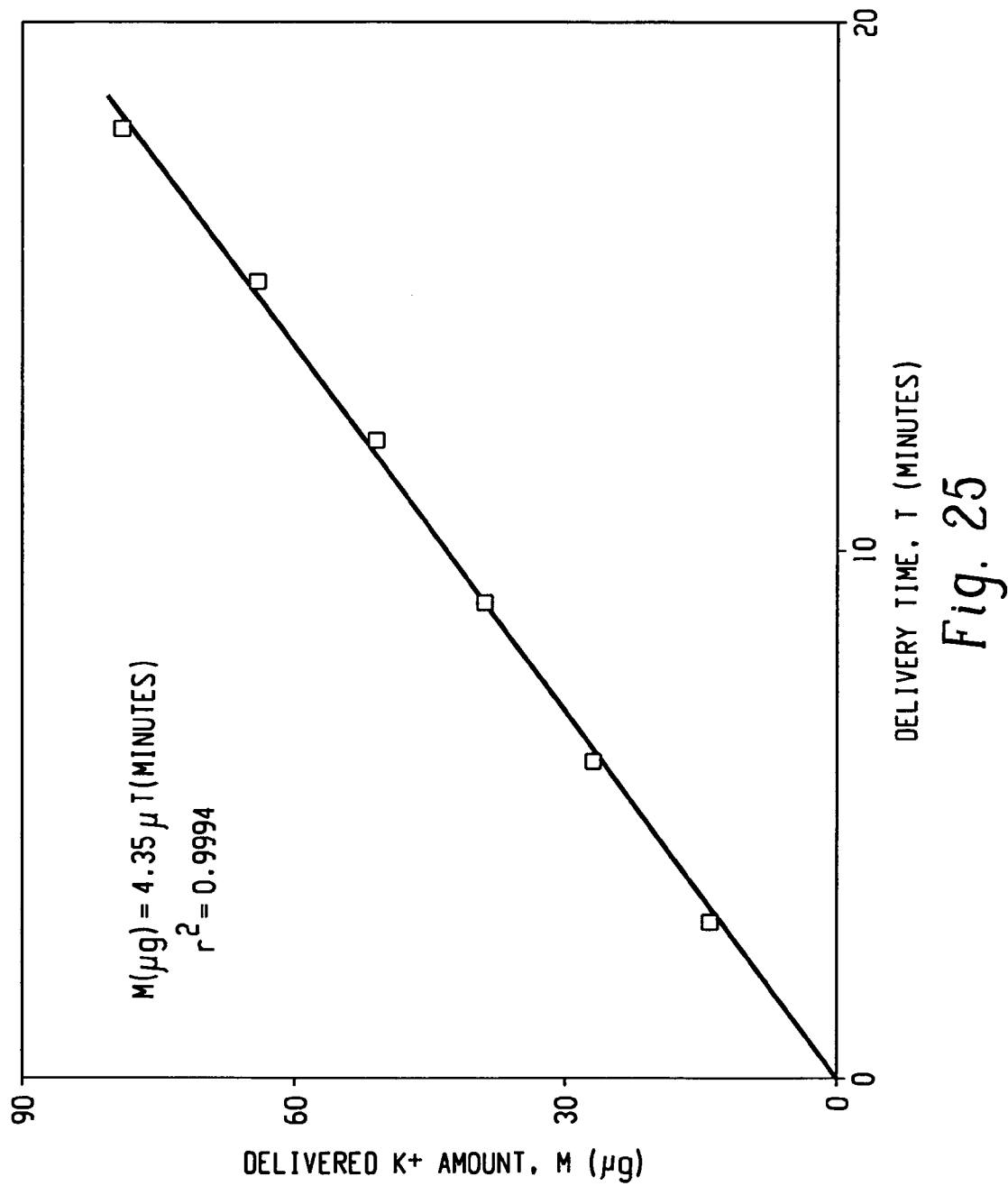
FIG. 25 is a plot of potassium ion concentration in a target solution over time.

Potassium ions were delivered from a burette of the type illustrated in FIGS. 8-11 in which the reagent concentration in the burette $C_b$ was 1M, the diameter d of each hole 36 was about 250 μm, and the number N of holes was 5. The delivered amount, in Moles was plotted against delivery time in minutes, as shown in FIG. 25. The linearity ($r^2$) was at least=0.999.

FIG. 25 can be used to calibrate a burette. Good linearity can justify using a linear calibration for R(t), but other cases are satisfactory as long as a reproducible delivery process is ensured. Knowing the desired amount of potassium ions to be delivered, the delivery time can be found from the plot.

Example 6

Comparison of a Diffusional Burette with a Conventional Pipette and Transfer Burette A burette of the type used in Example 5 was prepared with N=5. "Identical" deliveries were made with the burette to target solutions. The standard deviation was 0.7%, which was within the range of error of the potassium ion selective sensor used to measure the potassium ion concentration delivered (i.e., with more accurate detection techniques, the standard deviation could well have been lower). By comparison, a conventional method with a conventional burette, calibrated delivered solutions resulted in a standard deviation of 8.5% in final concentration, and a pipette tip system had a standard deviation in produced final delivery concentration of 8.8%.

The delivery time with the pre-prepared diffusional burette was generally less than ten minutes, which compares favorably with the time taken to prepare reagent solutions and load the transfer burette or pipette tip system and deliver the reagent.

Example 7

Effect of Pore Number and Stirring Speed on Delivery

Expt 1: Diffusional burettes were prepared as for FIGS. 8-11, one with a single hole (pore) of diameter=350 μm, the other with five holes of diameters=150 μm. Both burettes was filled with 1M KCL and 10 mM NaCl solution.

A target solution of 10 mL of 10 mM NaCl solution was prepared. Potassium ion in the target solution before delivery was zero (checked by ion-selective electrode that it is at least far less than $10^{-6}$ M).

A potassium ion selective electrode (based on Valinomycin) and a double junction type reference Ag/AgCl electrode were prepared. The output voltage was frequently calibrated by measuring the voltages on 10 mM NaCl plus 0, $10^{-6}$, $10^{-5}$, $10^{-4}$, $10^{-3}$ M KCl solutions, respectively. Outer and inner filling solution in the reference electrode was 10 mM and 3M NaCl solutions, respectively. Data processing was carried out using Matlab software.

A first experiment used fast stirring and simultaneous sensing. The electrodes and a temperature sensor (which is connected a to pH meter), were put in the 10 mL NaCl target solution in a 20 mL size beaker. A stirring bar was placed on the bottom of the beaker and rotated very fast (about 10 rotation/s). Then, the selected burette was placed in the target solution for 15-18 min. Output voltages from the electrodes were automatically transferred to and recorded in a PC every 20 seconds, with zero time corresponding to when the burette was put in the target solution. Voltages were translated to concentration using the calibration curve. Temperature in the solution increased 2.5° C. during the delivery due to simultaneous stirring.

Expt. 2: Experiments with burettes as described above in Expt. 1 were performed similar to those described above, but were carried out without continuous stirring over a 15 min delivery period. 10 mM of NaCl target solution was prepared in the 20 mL size beaker and the burette was put in it for 15 min. A stirring bar was placed on the bottom of the beaker, but it was rotated only before each concentration measurement for mixing up the delivered reagent in the solution. After 15 min of delivery, the burette was taken out from the solution, and the solution was stirred, and then the electrodes and temperature sensor were put in the solution to read the output voltage and temperature. This experiment was repeated 3-4 times to see reproducibility for both versions of burettes.

Voltages translated to concentration, and temperatures at measurement were:

5 Holes
(1st experiment) 1.0394e-004 M, 22.9° C.
(2nd experiment) 1.0054e-004 M, 22.7° C.
(3rd experiment) 1.0129e-004 M, 22.5° C.
($4^{th}$ experiment) 9.6178e-005 M, 22.4° C.
average: 1.0049e-004 M
standard deviation: 3.2232e-006 M (3.21%)

1 Hole
(1st experiment) 6.3477e-005 M, 22.4° C.
(2nd experiment) 5.4502e-005 M, 22.4° C.
(3rd experiment) 5.3057e-005 M, 22.4° C.
average: 5.7012e-005 M
standard deviation: 5.6454e-006 M (5.65%)

It was found that the limitation in reproducibility was largely accounted for by errors in measurement with the potassium electrode. This was checked by measuring the concentration of the same solution (0.1 mM KCl, 10 mM NaCl solution) 4 times with 15 min interval between measurements. Result showed ~3% of reproducibility error (std).

Expt. 3: A further experiment was carried out as for Expt. 2, but using slow stirring and sensing after every 15 min delivery. The procedure was the same as for Expt. 2, except that the stirring bar was rotated slowly (about 2rotations/sec) during delivery. Results showed reproducibility which was not as good as for Expt. 2. It was concluded that for the burettes studied, stirring by stirring bar may fluctuate the depletion field and cause less than optimal reproducibility of delivered reagent amount.

Expt. 4: A further experiment was carried out as for Expt. 2, without stirring using the 5 hole burette, to check for linearity. The burette put in the target solution for 3 minutes and taken out from the solution. The solution was stirred, and concentration was measured by electrodes. The same burette was then replaced in the measured solution for a further 3 minutes and the measurement procedure was repeated. Concentrations were measured after 0, 3, 6, 9, 12, 15 min deliveries. Between taking out from the solution and putting back into the solution, the burette was placed in a dummy 10 mM NaCl solution. The burette was washed with distilled water and wiped carefully before put back it into the solution.

Expt. 5: A further experiment was carried out with stirring and sensing with almost zero intervals for 15 min delivered solutions. Five 10 mM NaCl target solutions in the 20 mL size beakers were prepared. A five hole burette prepared as for Expt. 1 was put in each solution for 15 min. Care was taken to ensure air pockets did not form around the burette tip, by tilting the burette.

After each 15 min delivery, each solution was stored by covering the solution by parafilm. A stirring bar was placed on the bottom of each beaker, but it was rotated only during concentration measurement. After all 15 min deliveries were done, output voltages and temperatures from all 5 stored solutions were read. Voltages translated to concentration, and temperatures at measurement were:

5 Hole
(1st solution) −96.4 mV>>>8.54e-005 M, 22.4° C.
(2nd solution) −96.2 mV>>>8.61e-005 M, 22.4° C.
(3rd solution) −95.9 mV>>>8.71e-005 M, 22.4° C.
($4^{th}$ solution) −96.3 mV>>>8.58e-005 M, 22.4° C.
($5^{th}$ solution) −96.1 mV>>>8.64e-005 M, 22.4° C.
average: 8.6163e-005 M
standard deviation: 6.3057e-007 M (0.73%)

The reproducibility obtained was comparable to the measurement error of the potassium electrode. Thus the good delivery reproducibility of the burette is demonstrated.

Expt. 6: A further experiment was carried out as for Expt. 5, with no stirring and measurements taken after all deliveries. Nine beakers were prepared and heated to one of three temperatures. The delivered amount changed dramatically with temperature.

22.9° C.~65 µM
25.0° C.~70 µM
28.5° C.~90 µM

The diffusion coefficient, D, is understood to be linear with temperature, T, i.e., $D=kT$. However, the temperature dependence measured was not linear with T. It is proposed that convection may be responsible for the nonlinear increase of delivery rate of potassium with temperature.

Expt. 7: A further experiment was carried out to check the difference of reproducibility and delivery amount, between rotation (of the burette) and no rotation, and between stirring and no stirring using the following conditions Rotation (5 hole) 0.59-0.63A motor current.
Stirring; slow (stirring bar rotating 5-15 rps)
10 min delivery to 150 mL solution for each experiment.
The results for delivery amount are as follows:

| | | |
|---|---|---|
| 1. No stirring/No rotation: | mean: | 170 µM |
| | std: | 0.8% |
| 2. No stirring/Rotation: | mean: | 233 µM |
| | std: | 1.8% |
| 3. Stirring/No rotation: | mean: | 226 µM |
| | std: | 4.2% |
| 4. Stirring/Rotation: | mean: | 218 Mm |
| | std: | 5.0% |

It can be seen from these results that rotation of the burette tip in the target liquid increased the delivery rate by 37%. Although rotation was not entirely in axial alignment, and the electric current of the motor fluctuated somewhat (0.59-0.63A), the reproducibilty was still 1.8%. By more careful orientation of the rotational burette to achieve more uniform rpm and closer alignment, it can be expected that the results for rotation will be better than those obtained here.

Expt. 8. Comparison of conventional glassware with the diffusional burette.

A. Conventional Method

The procedure is as following. All necessary solutions (including 10 mM NaCl solution) were prepared with the following glassware: $1^{st}$ 100 mL glass measuring beaker; $2^{nd}$ 100 mL glass measuring beaker; $3^{rd}$ 10 mL glass measuring beaker; and 1 mL Transfer burette. The beakers were washed with pure water 3 times followed by washing by 10 mM NaCl solution 1 time. The beakers were filled with 10 mM NaCl solution. 372.8 g of KCL was weighed (mw 74.56) and added to the first beaker. 1 mL of the solution was transferred to the second beaker, using the transfer burette and shaken. 1 mL was transferred from the second to the third beaker in the same way. This was repeated five times. The procedure, from beginning to end, was also timed. The results for time, sensor voltage, and calculated concentration were as follows:

1st) 23 min05 sec/122.1 mV/49.3 µM
2nd) 19 min07 sec/124.0 mV/45.9 µM
3rd) 17 min38 sec/123.6 mV/46.6 µM
4th) 15 min05 sec/119.0 mV/55.5 µM
5th) 14 min12 sec/119.8 mV/53.8 µM
mean: 50.2 µM
std 8.5%

B. Diffusional Burette

Using a burette as described for Expt. 1, delivery was made into three solutions to determine a delivery rate. The delivery rate, taking the average of 3 results was 2.08 uM/min. From this, a delivery time for achieving about 50 µM was calculated as 2 min 24 sec. 5 beakers were prepared by washing with water 3 times, and 1 time with 10 mM NaCl solution. The beakers were filled with 10 mL of 10 mM NaCl solution. The tip of the burette was washed and wiped. The tip was contacted with each beaker solution for 2 min 24 sec. The procedure from beginning to end was timed with a stopwatch.

The results were as follows:
1st) 4 min34 sec/−121.8 mV/50.7 uM
2nd) 4 min11 sec/−122.0 mV/50.3 uM
3rd) 3 min59 sec/−122.6 mV 49.2 uM
4rd) 4 min02 sec/−122.3 mV 49.7 uM
5th) 3 min57 sec/−123.0 mV 48.4 uM
mean 49.7 uM
std 1.9%

As the delivery time (2 min 24 sec) was relatively short, and due to potential errors of the potassium, sensor the standard deviation was 1.9%. However, the results achieved with the diffusional burette were far superior to those achieved by the conventional method, both in terms of time taken and reproducibility. The reproducibility can be increased using an automated control of the up/down motion of the burette and use of an automated timer. The above experiments were carried out simply by hand and with a stopwatch.

The invention has been described with reference to the preferred embodiment. Obviously, modifications and alterations will occur to others upon reading and understanding the preceding detailed description. It is intended that the invention be construed as including all such modifications and alterations insofar as they come within the scope of the appended claims or the equivalents thereof.

Having thus described the preferred embodiments, the invention is now claimed to be:

1. A delivery device for delivering a reagent into a target material comprising:

a body which defines an interior chamber and a delivery port fluidly connected with the chamber, the chamber holding a reagent in solution;

a membrane in fluid communication with the chamber and the delivery port, through which reagent passes when the delivery port is in fluid communication with the target material, such that substantially no volume change occurs in the target material during delivery of the reagent to the target material; and a matrix material dispersed throughout the body and being in contact with the membrane, the reagent diffusing through the matrix material to the delivery port;

wherein the membrane includes a plurality of holes which define through passages through the membrane, each of the through passages being spaced apart from one another and separated by a rigid, impermeable portion of the membrane.

2. The delivery device of claim 1, wherein the body narrows intermediate the delivery port and the chamber.

3. The delivery device of claim 1, wherein the delivery port has a diameter of from about 10 to about 300 microns.

4. The delivery device of claim 1, wherein the membrane has a thickness of less than about 100 microns.

5. The delivery device of claim 4, wherein the reagent permeable membrane has a thickness of from about 2-50 microns.

6. The delivery device of claim 1, wherein the membrane is in or adjacent to the delivery port.

7. The delivery device of claim 1, wherein the holes have a diameter of less than about 300 microns.

8. The delivery device of claim 1, wherein the holes have a diameter of at least 100 nm.

9. The delivery device of claim 1, wherein the holes have a diameter of about 10-20 microns.

10. The delivery device of claim 1, wherein the holes are filled with a reagent permeable material.

11. The delivery device of claim 1, further including an agitator which agitates at least a portion of the body.

12. The delivery device of claim 1, further including a heating or cooling device which selectively heats or cools at least a portion of the body.

13. The delivery device of claim 1, further including a control system which calculates a delivery time for preparing a target solution of a preselected reagent concentration and volume.

14. The delivery device of claim 1, wherein the target material comprises a liquid.

15. The delivery device of claim 1, further including a hydrophobic coating on an exterior surface of the body.

16. The delivery device of claim 1, wherein the reagent diffuses from the delivery device into the target liquid with substantially no volume change in the target liquid.

* * * * *